United States Patent
Zhan et al.

(10) Patent No.: US 11,103,509 B2
(45) Date of Patent: Aug. 31, 2021

(54) METHODS OF TREATING PAIN AND/OR INFLAMMATORY DISORDERS USING LAPATINIB

(71) Applicant: University of Kentucky Research Foundation, Lexington, KY (US)

(72) Inventors: Chang-Guo Zhan, Lexington, KY (US); Fang Zheng, Lexington, KY (US); Shuo Zhou, Lexington, KY (US); Ziyuan Zhou, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/675,980

(22) Filed: Nov. 6, 2019

(65) Prior Publication Data

US 2020/0138818 A1    May 7, 2020

Related U.S. Application Data

(60) Provisional application No. 62/756,961, filed on Nov. 7, 2018.

(51) Int. Cl.
*A61K 31/517* (2006.01)
*A61P 23/00* (2006.01)

(52) U.S. Cl.
CPC ............ *A61K 31/517* (2013.01); *A61P 23/00* (2018.01)

(58) Field of Classification Search
CPC .............................. A61K 31/517; A61P 23/00
See application file for complete search history.

(56) References Cited

U.S. PATENT DOCUMENTS

2014/0134161 A1* 5/2014 Kersten .............. A61K 39/3955
424/133.1

OTHER PUBLICATIONS

Hamza, A.; Tong, M.; AbdulHameed, M. D.; Liu, J.; Goren, A. C.; Tai, H. H.; Zhan, C. G., Understanding microscopic binding of human microsomal prostaglandin E synthase-1 (mPGES-1) trimer with substrate PGH2 and cofactor GSH: insights from computational alanine scanning and site-directed mutagenesis. J Phys Chem B. 2010, 114 (16), 5605-16.
Huang, X. Q.; Yan, W. L.; Gao, D. Q.; Tong, M.; Tai, H.-H.; Zhan, C.-G., Structural and functional characterization of human microsomal prostaglandin E synthase-1 by computational modeling and site-directed mutagenesis. Bioorg. Med. Chem. 2006, 14, 3553-3562.
Hamza, A.; Zhao, X.; Tong, M.; Tai, H. H.; Zhan, C. G., Novel human mPGES-1 inhibitors identified through structure-based virtual screening. Bioorg. Med. Chem. 2011, 19 (20), 6077-86.
Ding, H.; Czoty, P. W.; Kiguchi, N.; Cami-Kobeci, G.; Sukhtankar, D. D.; Nader, M. A.; Husbands, S. M.; Ko, M.-C., A novel orvinol analog, BU08028, as a safe opioid analgesic without abuse liability in primates. Proc. Natl Acad. Sci. USA 2016, 113, pp. E5511-E5518.
Hamza, A.; Zhao, X.; Tong, M.; Tai, H.-H.; Zhan, C.-G., Novel human mPGES-1 inhibitors identified through structure-based virtual screening. Bioorg. Med. Chem. 2011, 19, 6077-6086.
Zhou, Z.; Yuan, Y.; Zhou, S.; Ding, K.; Zheng, F.; Zhan, C.-G., Selective inhibitors of human mPGES-1 from structure-based computational screening. Biorg. Med. Chem. Letters 2017, 27, 3739-3743.
Ding, K.; Zhou, Z.; Zhou, S.; Yuan, Y.; Kim, K.; Zhang, T.; Zheng, X.; Zheng, F.; Zhan, C.-G., Design, synthesis, and discovery of 5-((1,3-diphenyl-1H-pyrazol-4-yl)methylene)pyrimidine-2,4,6(1H,3H,5H)-triones and related derivatives as novel inhibitors of mPGES-1. Bioorg. Med. Chem. Letters 2018, 28, 858-862.
Zhan, C.-G.; Zheng, F.; Ding, K.; Zhou, Z., PCT/US2017/039785: No. WO2018/005660. "Prostaglandin E Synthase Inhibitors and Methods for Utilizing the Same" (World Patent filed on Jun. 28, 2017). 2017.
Ding, K.; Zhou, Z.; Hou, S.; Yuan, Y.; Zhou, S.; Zheng, X.; Chen, J.; Loftin, C.; Zheng, F.; Zhan, C.-G., Structure-based discovery of mPGES-1 inhibitors suitable for preclinical testing in wild-type mice as a new generation of anti-inflammatory drugs. Scientific Reports, Aug. 2018, 5205. doi:10.1038/s41598-018-23482-4.
Koeberle, A.; Laufer, S. A.; Werz, O., Design and Development of Microsomal Prostaglandin E2 Synthase-1 Inhibitors: Challenges and Future Directions. J. Med. Chem. 2016, 59, 5970-5986.
Meunier; L.; Larrey, D., Recent Advances in Hepatotoxicity of Non Steroidal Anti-Inflammatory Drugs. Ann. Hepatol. 2018, 17, 187-191.
Strawson, J., Nonsteroidal anti-inflammatory drugs and cancer pain. Curr. Opin Support Palliat Care 2018, doi: 10.1097/SPC.0000000000000332 [Epub ahead of print: Feb. 9, 2018].
Thomas, K.; Moody, T. W.; Jensen, R. T.; Tong, J.; Rayner, C. L.; Barnett, N. L.; Fairfull-Smith, K. E.; Ridnour, L. A.; Wink, D. A.; Bottle, S. E., Design, synthesis and biological evaluation of hybrid nitroxide-based non-steroidal anti-inflammatory drugs. Eur. J. Med. Chem. 2018, 147, 34-47.
Kudo, I.; Murakami, M., Prostaglandin E synthase, a terminal enzyme for prostaglandin E-2 biosynthesis. Journal of Biochemistry and Molecular Biology 2005, 38 (6), 633-638.
Serhan, C. N.; Levy, B., Success of prostaglandin E-2 in structure-function is a challenge for structure-based therapeutics. Proceedings of the National Academy of Sciences of the United States of America 2003, 100 (15), 8609-8611.
Radmark, O.; Samuelsson, B., Microsomal prostaglandin E synthase-1 and 5-lipoxygenase: potential drug targets in cancer. J. Intern. Med. 2010, 268, 5-14.
Hanaka, H.; Pawelzik, S.-C.; Johnsen, J. I.; Rakonjac, M.; Terawaki, K.; Rasmuson, A.; Sveinbjornsson, B.; Schumacher, M. C.; Hamberg, M.; Samuelsson, B.; Jakobsson, P.-J.; Kogner, P.; Rådmark, O., Microsomal prostaglandin E synthase 1 determines tumor growth in vivo of prostate and lung cancer cells. Proc. Natl. Acad. Sci. USA 2009, 106, 18757-18762.

(Continued)

*Primary Examiner* — Timothy R Rozof
(74) *Attorney, Agent, or Firm* — Stites & Harbison PLLC; Mandy Wilson Decker

(57) ABSTRACT

A method of treating pain is disclosed, which involves administering an effective amount of lapatinib or a pharmaceutically-acceptable salt thereof to a subject in need of treatment for pain.

17 Claims, 5 Drawing Sheets

(56) References Cited

OTHER PUBLICATIONS

Koeberle, A.; Werz, O., Perspective of microsomal prostaglandin E2 synthase-1 as drug target in inflammation-related disorders. Biochem. Pharmacol. 2015, 98, 1-15.
Fahmi, H., MPGES-1 as a novel target for arthritis. Current Opinion in Rheumatology 2004, 16 (5), 623-627.
Tanioka, T.; Nakatani, Y.; Semmyo, N.; Murakami, M.; Kudo, I., Molecular identification of cytosolic prostaglandin E2 synthase that is functionally coupled with cyclooxygenase-1 in immediate prostaglandin E2 biosynthesis. J. Biol. Chem. 2000, 275 (42), 32775-82.
Cheng, Y.; Wang, M.; Yu, Y.; Lawson, J.; Funk, C. D.; FitzGerald, G. A., Cyclooxygenases, microsomal prostaglandin E synthase-1, and cardiovascular function. Journal of Clinical Investigation 2006, 116 (5), 1391-1399.
Engblom, D.; Saha, S.; Engstrom, L.; Westman, M.; Audoly, L. P.; Jakobsson, P. J.; Blomqvist, A., Microsomal prostaglandin E synthase-1 is the central switch during immune-induced pyresis. Nature Neuroscience, Jun. 2003, (11), 1137-1138.
Trebino, C. E.; Stock, J. L.; Gibbons, C. P.; Naiman, B. M.; Wachtmann, T. S.; Umland, J. P.; Pandher, K.; Lapointe, J. M.; Saha, S.; Roach, M. L.; Carter, D.; Thomas, N. A.; Durtschi, B. A.; McNeish, J. D.; Hambor, J. E.; Jakobsson, P. J.; Carty, T. J.; Perez, J. R.; Audoly, L. P., Impaired inflammatory and pain responses in mice lacking an inducible prostaglandin E synthase. Proceedings of the National Academy of Sciences of the United States of America 2003, 100 (15), 9044-9049.
Ikeda-Matsuo, Y.; Ota, A.; Fukada, T.; Uematsu, S.; Akira, S.; Sasaki, Y., Microsomal prostaglandin E synthase-1 is a critical factor of stroke-reperfusion injury. Proceedings of the National Academy of Sciences of the United States of America 2006, 103 (31), 11790-11795.
Friesen, R. W.; Mancini, J. A., Microsomal prostaglandin E-2 synthase-1 (mPGES-1): A novel anti-inflammatory therapeutic target. Journal of medicinal chemistry 2008, 51 (14), 4059-4067.
Schiffler, M. A.; Antonysamy, S.; Bhattachar, S. N.; Campanale, K. M.; Chandrasekhar, S.; Condon, B.; Desai, P. V.; Fisher, M. J.; Groshong, C.; Harvey, A.; Hickey, M. J.; Hughes, N. E.; Jones, S. A.; Kim, E. J.; Kuklish, S. L.; Luz, J. G.; Norman, B. H.; Rathmell, R. E.; Rizzo, J. R.; Seng, T. W.; Thibodeaux, S. J.; Woods, T. A.; York, J. S.; Yu, X. P., Discovery and Characterization of 2-Acylaminoimidazole Microsomal Prostaglandin E Synthase-1 Inhibitors. Journal of medicinal chemistry 2016, 59 (1), 194-205.
Hieke, M.; Greiner, C.; Dittrich, M.; Reisen, F.; Schneider, G.; Schubert-Zsilavecz, M.; Werz, O., Discovery and biological evaluation of a novel class of dual microsomal prostaglandin E2 synthase-1/5-lipoxygenase inhibitors based on 2-[(4,6-diphenethoxypyrimidin-2-yl)thio]hexanoic acid. Journal of medicinal chemistry 2011, 54 (13), 4490-507.
Hanke, T.; Dehm, F.; Liening, S.; Popella, S. D.; Maczewsky, J.; Pillong, M.; Kunze, J.; Weinigel, C.; Barz, D.; Kaiser, A.; Wurglics, M.; Lammerhofer, M.; Schneider, G.; Sautebin, L.; Schubert-Zsilavecz, M.; Werz, O., Aminothiazole-featured pinnixic acid derivatives as dual 5-lipoxygenase and microsomal prostaglandin E2 synthase-1 inhibitors with improved potency and efficiency in vivo. Journal of medicinal chemistry 2013, 56 (22), 9031-44.
Terracciano, S.; Lauro, G.; Strocchia, M.; Fischer, K.; Werz, O.; Riccio, R.; Bruno, I.; Bifulco, G., Structural Insights for the Optimization of Dihydropyrimidin-2(1H)-one Based mPGES-1 Inhibitors. ACS medicinal chemistry letters, Jun. 2015, (2), 187-91.
Shiro, T.; Kakiguchi, K.; Takahashi, H.; Nagata, H.; Tobe, M., 7-Phenyl-imidazoquinolin-4(5H)-one derivatives as selective and orally available mPGES-1 inhibitors. Bioorganic & medicinal chemistry 2013, 21 (11), 2868-78.
Shiro, T.; Kakiguchi, K.; Takahashi, H.; Nagata, H.; Tobe, M., Synthesis and biological evaluation of substituted imidazoquinoline derivatives as mPGES-1 inhibitors. Bioorganic & medicinal chemistry 2013, 21 (7), 2068-78.
Shiro, T.; Takahashi, H.; Kakiguchi, K.; Inoue, Y.; Masuda, K.; Nagata, H.; Tobe, M., Synthesis and SAR study of imidazoquinolines as a novel structural class of microsomal prostaglandin E(2) synthase-1 inhibitors. Bioorg Med Chem Lett 2012, 22 (1), 285-8.
Liedtke, A. J.; Keck, P. R.; Lehmann, F.; Koeberle, A.; Werz, O.; Laufer, S. A., Arylpyrrolizines as inhibitors of microsomal prostaglandin E2 synthase-1 (mPGES-1) or as dual inhibitors of mPGES-1 and 5-lipoxygenase (5-LOX). Journal of medicinal chemistry 2009, 52 (15), 4968-72.
Shang, E.; Wu, Y.; Liu, P.; Liu, Y.; Zhu, W.; Deng, X.; He, C.; He, S.; Li, C.; Lai, L., Benzo[d]isothiazole 1,1-dioxide derivatives as dual functional inhibitors of 5-lipoxygenase and microsomal prostaglandin E(2) synthase-1. Bioorg Med Chem Lett 2014, 24 (12), 2764-7.
Wu, T. Y.; Juteau, H.; Ducharme, Y.; Friesen, R. W.; Guiral, S.; Dufresne, L.; Poirier, H.; Salem, M.; Riendeau, D.; Mancini, J.; Brideau, C., Biarylimidazoles as inhibitors of microsomal prostaglandin E2 synthase-1. Bioorg Med Chem Lett 2010, 20 (23), 6978-82.
Wiegard, A.; Hanekamp, W.; Griessbach, K.; Fabian, J.; Lehr, M., Pyrrole alkanoic acid derivatives as nuisance inhibitors of microsomal prostaglandin E2 synthase-1. European journal of medicinal chemistry 2012, 48, 153-63.
Chini, M. G.; De Simone, R.; Bruno, I.; Riccio, R.; Dehm, F.; Weinigel, C.; Barz, D.; Werz, O.; Bifulco, G., Design and synthesis of a second series of triazole-based compounds as potent dual mPGES-1 and 5-lipoxygenase inhibitors. European journal of medicinal chemistry 2012, 54, 311-23.
Giroux, A.; Boulet, L.; Brideau, C.; Chau, A.; Claveau, D.; Cote, B.; Ethier, D.; Frenette, R.; Gagnon, M.; Guay, J.; Guiral, S.; Mancini, J.; Martins, E.; Masse, F.; Methot, N.; Riendeau, D.; Rubin, J.; Xu, D.; Yu, H.; Ducharme, Y.; Friesen, R. W., Discovery of disubstituted phenanthrene imidazoles as potent, selective and orally active mPGES-1 inhibitors. Bioorg Med Chem Lett 2009, 19 (20), 5837-41.
Xu, D.; Rowland, S. E.; Clark, P.; Giroux, A.; Cote, B.; Guiral, S.; Salem, M.; Ducharme, Y.; Friesen, R. W.; Methot, N.; Mancini, J.; Audoly, L.; Riendeau, D., MF63 [2-(6-chloro-1H-phenanthro[9,10-d]imidazol-2-yl)-isophthalonitrile], a selective microsomal prostaglandin E synthase-1 inhibitor, relieves pyresis and pain in preclinical models of inflammation. J. Pharmacol. Exp. Ther. 2008, 326 (3), 754-63.
Lee, K.; Pham, V. C.; Choi, M. J.; Kim, K. J.; Lee, K. T.; Han, S. G.; Yu, Y. G.; Lee, J. Y., Fragment-based discovery of novel and selective mPGES-1 inhibitors Part 1: identification of sulfonamido-1,2,3-triazole-4,5-dicarboxylic acid. Bioorg Med Chem Lett 2013, 23 (1), 75-80.
Cote, B.; Boulet, L.; Brideau, C.; Claveau, D.; Ethier, D.; Frenette, R.; Gagnon, M.; Giroux, A.; Guay, J.; Guiral, S.; Mancini, J.; Martins, E.; Masse, F.; Methot, N.; Riendeau, D.; Rubin, J.; Xu, D.; Yu, H.; Ducharme, Y.; Friesen, R. W., Substituted phenanthrene imidazoles as potent, selective, and orally active mPGES-1 inhibitors. Bioorg Med Chem Lett 2007, 17 (24), 6816-20.
Riendeau, D.; Aspiotis, R.; Ethier, D.; Gareau, Y.; Grimm, E. L.; Guay, J.; Guiral, S.; Juteau, H.; Mancini, J. A.; Methot, N.; Rubin, J.; Friesen, R. W., Inhibitors of the inducible microsomal prostaglandin E2 synthase (mPGES-1) derived from MK-886. Bioorg Med Chem Lett 2005, 15 (14), 3352-5.
Bruno, A.; Di Francesco, L.; Coletta, I.; Mangano, G.; Alisi, M. A.; Polenzani, L.; Milanese, C.; Anzellotti, P.; Ricciotti, E.; Dovizio, M.; Di Francesco, A.; Tacconelli, S.; Capone, M. L.; Patrignani, P., Effects of AF3442 [N-(9-ethyl-9H-carbazol-3-yl)-2-(trifluoromethyl)benzamide], a novel inhibitor of human microsomal prostaglandin E synthase-1, on prostanoid biosynthesis in human monocytes in vitro. Biochem Pharmacol 2010, 79 (7), 974-81.
Koeberle, A.; Haberl, E. M.; Rossi, A.; Pergola, C.; Dehm, F.; Northoff, H.; Troschuetz, R.; Sautebin, L.; Werz, O., Discovery of benzo[g]indol-3-carboxylates as potent inhibitors of microsomal prostaglandin E(2) synthase-1. Bioorganic & medicinal chemistry 2009, 17 (23), 7924-32.
Walker, D. P.; Arhancet, G. B.; Lu, H. F.; Heasley, S. E.; Metz, S.; Kablaoui, N. M.; Franco, F. M.; Hanau, C. E.; Scholten, J. A.; Springer, J. R.; Fobian, Y. M.; Carter, J. S.; Xing, L.; Yang, S.; Shaffer, A. F.; Jerome, G. M.; Baratta, M. T.; Moore, W. M.; Vazquez, M. L., Synthesis and biological evaluation of substituted

(56) References Cited

OTHER PUBLICATIONS benzoxazoles as inhibitors of mPGES-1: use of a conformation-based hypothesis to facilitate compound design. Bioorg Med Chem Lett 2013, 23 (4), 1120-6.

Wang, J.; Limburg, D.; Carter, J.; Mbalaviele, G.; Gierse, J.; Vazquez, M., Selective inducible microsomal prostaglandin E(2) synthase-1 (mPGES-1) inhibitors derived from an oxicam template. Bioorg Med Chem Lett 2010, 20(5), 1604-9.

Jin, Y.; Smith, C. L.; Hu, L.; Campanale, K. M.; Stoltz, R.; Huffman, L. G., Jr.; McNeamey, T. A.; Yang, X. Y.; Ackermann, B. L.; Dean, R.; Regev, A.; Landschulz, W., Pharmacodynamic comparison of LY3023703, a novel microsomal prostaglandin e synthase 1 inhibitor, with celecoxib. Clinical pharmacology and therapeutics 2016, 99 (3), 274-84.

Sjogren, T.; Nord, J.; Ek, M.; Johansson, P.; Liu, G.; Geschwindner, S., Crystal structure of microsomal prostaglandin E2 synthase provides insight into diversity in the MAPEG superfamily. Proceedings of the National Academy of Sciences of the United States of America 2013, 110 (10), 3806-11.

Bence, A. K.; Anderson, E. B.; Halepota, M. A.; Doukas, M. A.; DeSimone, P. A.; Davis, G. A.; Smith, D. A.; Koch, K. M.; Stead, A. G.; Mangum, S.; Bowen, C. J.; Spector, N. L.; Hsieh, S.; Adams, V. R., Phase I pharmacokinetic studies evaluating single and multiple doses of oral GW572016, a dual EGFR-ErbB2 inhibitor, in healthy subjects. Invest New Drugs 2005, 23 (1), 39-49.

Hudachek, S. F.; Gustafson, D. L., Physiologically based pharmacokinetic model of lapatinib developed in mice and scaled to humans. J Pharmacokinet Pharmacodyn 2013, 40 (2), 157-76.

Kaufman, B.; Wu, Y.; Amonkar, M. M.; Sherrill, B.; Bachelot, T.; Salazar, V.; Viens, P.; Johnston, S., Impact of lapatinib monotherapy on QOL and pain symptoms in patients with HER2+ relapsed or refractory inflammatory breast cancer. Curr Med Res Opin 2010, 26 (5), 1065-73.

Goss, P. E.; Smith, I. E.; O'Shaughnessy, J.; Ejlertsen, B.; Kaufmann, M.; Boyle, F.; Buzdar, A. U.; Fumoleau, P.; Gradishar, W.; Martin, M.; Moy, B.; Piccart-Gebhart, M.; Pritchard, K. I.; Lindquist, D.; Chavarri-Guerra, Y.; Aktan, G.; Rappold, E.; Williams, L. S.; Finkelstein, D. M.; investigators, T., Adjuvant lapatinib for women with early-stage HER2-positive breast cancer: a randomised, controlled, phase 3 trial. The Lancet. Oncology 2013, 14 (1), 88-96.

Zhou, Z.; Yuan, Y.; Zhou, S.; Ding, K.; Zheng, F.; Zhan, C. G., Selective inhibitors of human mPGES-1 from structure-based computational screening. Bioorg. Med. Chem. Lett. 2017, 27 (16), 3739-3743.

* cited by examiner

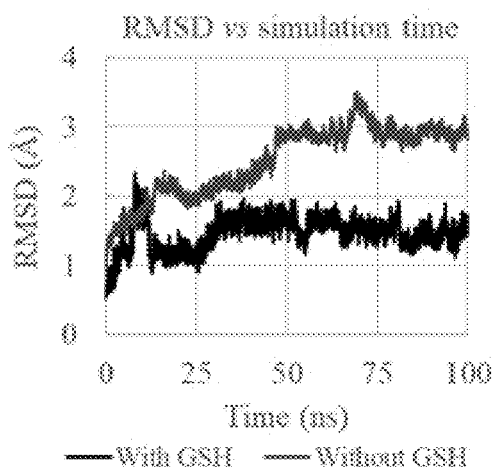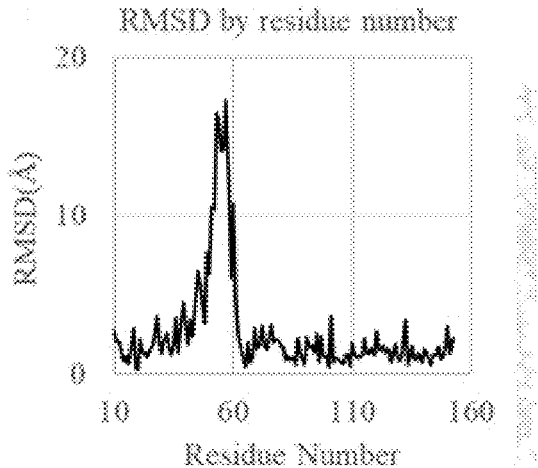
FIG. 1A  FIG. 1B
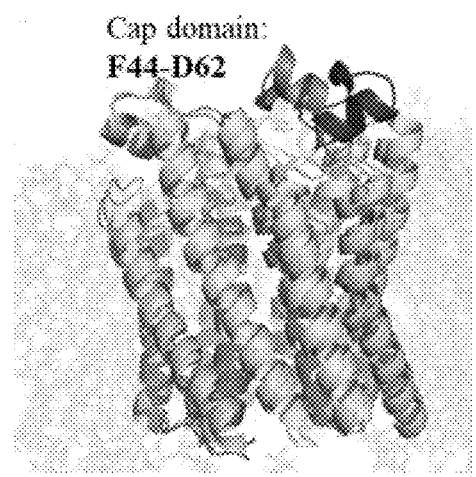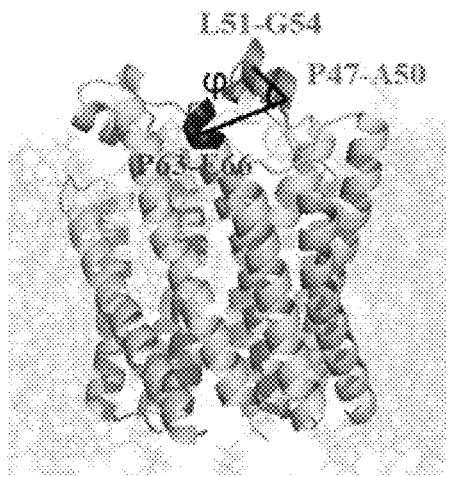
FIG. 1C  FIG. 1D
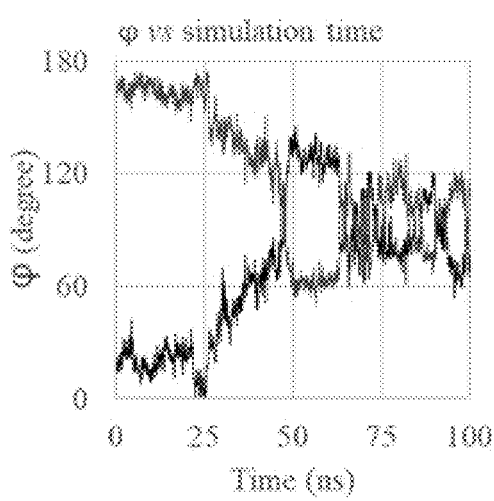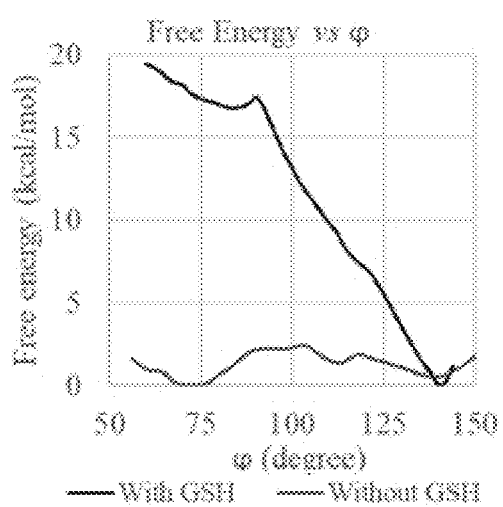
FIG. 1E  FIG. 1F

METHODS OF TREATING PAIN AND/OR INFLAMMATORY DISORDERS USING LAPATINIB

RELATED APPLICATIONS

This application claims priority from U.S. Provisional Application Ser. No. 62/756,961 filed Nov. 7, 2018, the entire disclosure of which is incorporated herein by this reference.

GOVERNMENT INTEREST

This invention was made with government support under grant number CHE-1111761 awarded by the National Science Foundation. The government has certain rights in the invention.

TECHNICAL FIELD

The presently-disclosed subject matter relates to the identification of Lapatinib as a prostaglandin E synthase-1 (mPGES-1) inhibitor, and using Lapatinib to treat pain in a subject in need thereof.

INTRODUCTION

Approximately 25.5 million adults suffer from chronic pain, and opioids are often prescribed; this can lead to opioid misuse and opioid use disorders (OUDs).[1] As one of the most devastating consequences of opioid misuse, opioid overdose can produce respiratory depression and death. Drug overdose is the leading cause of accidental death in the United States. It has been estimated that there were over 60,000 drug overdose deaths in 2016, including 20,101 overdose deaths related to prescription pain relievers and 12,990 overdose deaths related to heroin.[2]

It has also been reported that more than 2 million Americans suffer from OUDs, and for many their OUD began with prescribed opioids. For example, 80% of recent heroin initiates reported that they began their opioid use through the use of prescription opioids.[3] The prevalence of prescription opioid abuse is similar among men and women. Those who misuse the prescription opioids most often obtain them from friends and family either through sharing or theft. When they are no longer able to get prescription opioids, they start to use illicit opioids (e.g. heroin, fentanyl or its analogs, or a heroin/fentanyl mixture) that are relatively cheap and easy to obtain. Based on the known connection between the prescription opioid use and opioid use disorder/overdose, it is highly desirable to explore non-addictive pain medications that can be used as alternatives to opioids for pain relief to prevent the initiation or progression of OUDs and prevent overdoses.

As is well known, opioids are a class of analgesics with the capacity to deliver pain relief by activating opioid receptors, particularly µ-opioid receptors. Unfortunately, while effective as analgesics, opioids are also associated with abuse and physical dependence potential. Currently available opioids also have other side effects including constipation, sexual dysfunction and depression.[4] The other major class of analgesics in clinical use are nonsteroidal anti-inflammatory drugs (NSAIDs) that block cyclooxygenase (COX) enzymes (including both COX-1 and COX-2 that are necessary for biosynthesis of prostaglandin E2 or PGE2), and these are not associated with abuse potential. Unfortunately, the use of the currently available NSAIDs (COX-1/2 inhibitors) have significant cardiovascular and cerebrovascular risks that have limited their utilization.[5-6]

Notably, the two classes of pain medications (NSAIDs and opioids) target different stages of the primary physiological process of pain. In general, pain starts from tissue damage/injury and the corresponding inflammation response, and the two classes of the pain medications are closely related in the primary mechanism of pain. Specifically, tissue damage induces spinal release of $PGE_2$ (the principal pro-inflammatory agent), which acts on $EP_2$ receptors expressed by excitatory interneurons and projection neurons in the superficial dorsal horn and stimulates adenylate cyclase which is the enzyme producing 3',5'-cyclic adenosine monophosphate (cAMP, an intracellular second messenger).[7] Resultant stimulation of the cAMP-dependent pathway phosphorylates GlyRα3 glycine receptor subunits, rendering the neurons unresponsive to the inhibitory effects of glycine.[7-8] For the mechanistic connection, opioids activate opioid receptors that inhibit adenylate cyclase and, thus, decrease the cAMP signaling.[9] So, the two classes of pain medications target different stages within the primary mechanism of pain. NSAIDs target the upstream process of pain (pro-inflammatory agent $PGE_2$ production, the primary cause of pain), whereas opioids target the downstream process of pain (one of the consequences of pro-inflammatory agent $PGE_2$ production).

Given the currently available medications, a subject in need of treatment for pain is faced with a dilemma: "When you consider or are prescribed a pain medication, think about all the possible complications that could arise from taking it. You may be risking a heart attack or stroke, or living with an addiction to (often expensive) pain medication."[10]

In this regard, there have been extensive efforts to identify non-addictive opioids or alternative opioid analgesics with reduced abuse liability. As is well known, opioid receptors include µ, δ, and κ and nociception subtypes. The reported search for desirable non-addictive opioids or alternative opioid analgesics with reduced abuse liability either targets a specific opioid receptor subtype, such as a µ-opioid receptor[11] or κ-opioid receptor,[12] or multiple subtypes, such as µ- and δ-opioid receptors[13] or µ-opioid receptor and nociceptor.[14]

There is interest in development of a non-opioid pain reliever, i.e. an improved NSAID without any abuse liability. On the other hand, it is extremely challenging to identify an effective non-opioid pain reliever without serious side effects. In fact, there have been similarly extensive efforts in search for safer NSAIDs.[15-23]

As is well known, biosynthesis[24] of $PGE_2$ (the principal pro-inflammatory prostanoid[25-28]) starts from arachidonic acid (AA). COX-1/2 converts AA to prostaglandin H2 ($PGH_2$),[24] and prostaglandin E synthase (PGES) transforms $PGH_2$ to $PGE_2$.[29] Microsomal PGES (particularly mPGES-1) is induced strongly in inflammatory state, while cytosolic PGES (cPGES, which provides basal level of $PGE_2$ for physiological homeostasis[30]) remains unchanged.

The 1$^{st}$ generation of NSAIDs, such as aspirin and ibuprofen used to treat pain and reduce fever or inflammation, are weak inhibitors (with only micromolar $IC_{50}$) of both COX-1 and COX-2 without selectivity, and the 2$^{nd}$ generation of NSAIDs, including celecoxib, rofecoxib, and valdecoxib, selectively inhibit COX-2 (with nanomolar $IC_{50}$). The COX-2 specific inhibitors still have a number of serious side effects, such as increasing the risk of fatal heart attack or stroke and causing stomach or intestinal bleeding. The serious side effects led to withdrawal of rofecoxib and valdecoxib, although celecoxib still remains in clinical use. The serious side effects are because the synthesis of all physiologically-needed prostaglandins downstream of $PGH_2$ are inhibited by the action of the COX-1/2 inhibitors. For example, blocking the production of prostaglandin-$I_2$ ($PGI_2$) will cause significant cardiovascular problems.[31] So, clinical use of a potent COX-1/2 inhibitor, such as celecoxib, at a sufficiently effective dose must be associated with serious side effects.

As an inducible enzyme, mPGES-1 is a more promising, ideal target for anti-inflammatory drugs, because the mPGES-1 inhibition will only block the $PGE_2$ production without affecting the production of $PGI_2$ and other prostaglandins, as confirmed by reported knock-out studies.[32-33] The human mPGES-1 protein is related to a variety of diseases associated with inflammation and pain. Unlike the COX-1/2 inhibition, inhibition of terminal enzyme mPGES-1 will only block the production of $PGE_2$ without affecting the normal production of other prostaglandins including $PGI_2$. Reported knock-out studies identified mPGES-1 as an essential central switch in pyresis.[32] The mPGES-1 knock-out studies also revealed a decrease in inflammatory response in a collagen-induced arthritis model.[33] In contrast to COX-2, mPGES-1-deficient mice were reported to be viable, fertile, and have a normal phenotype.[33] Ischemic stroke induced in mPGES-1 null mice was reported to show significant reduction in the infarct size and volume.[34-35] Thus, mPGES-1 inhibitors are expected to retain the anti-inflammatory and pain-relieving effects of COX-1/2 inhibitors, but without the side effects caused by the COX-1/2 inhibition.

As the present inventors contemplate, compared to clinically-available traditional NSAIDs that inhibit COX-1/2, a highly selective mPGES-1 inhibitor would be a much more effective analgesic in practical clinical use. This is because the mPGES-1 inhibitor directly blocks generation of the pro-inflammatory agent ($PGE_2$) itself. In addition, unlike COX-1/2, mPGES-1 can be inhibited completely without any side effects. Accordingly, dose could be safely escalated, if necessary, to achieve the desirable efficacy, whereas inhibiting COX-1/2 is always associated with unwanted side effects.

Further, when a highly selective mPGES-1 inhibitor is used to selectively inhibit the production of pro-inflammatory agent $PGE_2$ for pain relief, there will be no elevation of adenylate cyclase, which is the enzyme producing cAMP. Thus, there would be no need to use an opioid to activate opioid receptors for inhibiting adenylate cyclase if such an mPGES-1 inhibitor became clinically available for pain relief. In addition, a high dose of opioid-stimulated complete inhibition of the global adenylate cyclase activity would also block the cAMP signaling in the normal physiological process and, thus, could lead to serious toxicity or lethality. Accordingly, if a potent mPGES-1 inhibitor became clinically-available, it would be superior to both traditional NSAIDs (COX-1/2 inhibitors) and opioids in terms of both the efficacy and safety.

Various mPGES-1 inhibitors have been reported in the literature.[36-57] Unfortunately, almost all of the previously reported human mPGES-1 inhibitors are inactive against mouse or rat mPGES-1, which prevents using well-established mouse/rat models of inflammation and pain for pre-clinical studies.[19] Hence, it would be extremely challenging for mPGES-1-based drug development to follow the traditional drug discovery and development pathway, which starts from lead identification and optimization based on various in vitro and in vivo assays in terms of the activity and toxicity etc.

Therefore, there remains a need for unique, less addictive or non-addictive, and safer pain medications, and new strategies for identifying and validate suitable mPGES-1 inhibitors for use in treating pain.

SUMMARY

The presently-disclosed subject matter meets some or all of the above-identified needs, as will become evident to those of ordinary skill in the art after a study of information provided in this document.

The presently-disclosed subject matter includes a new strategy for identifying FDA-approved drugs suitable for use as effective analgesics. The presently-disclosed subject matter also includes methods of using Lapatinib to treat pain.

The system for identifying suitable for use as effective analgesics is referred to herein as "DREAM-in-CDM" (Drug Repurposing Effort Applying Integrated Modeling-in vitro/vivo-Clinical Data Mining). The DREAM-in-CDM approach consists of three steps: (1) computational modeling to predict which FDA-approved drugs may favorably bind with the desirable drug target (mPGES-1 in this project); (2) in vitro and/or in vivo assays to validate the computational predictions; (3) clinical data mining to confirm the efficacy associated with the required clinical end points for the new therapeutic indication. By using the DREAM-in-CDM approach, the present-inventors identified lapatinib as a human mPGES-1 inhibitor which can be used to significantly relief various types of pain.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1A-1F. (FIG. 1A) Stability of mPGES-1 in 100 ns MD simulation of mPGES-1 with and without GSH. (FIG. 1B) RMSD of each residue in the MD-simulated mPGES-1 structure without co-factor GSH. (FIG. 1C) The cap domain in its "closed" (black) and "open" (dark grey) conformation during the MD simulation. The other part of mPGES-1 is showed in grey cartoon. (FIG. 1D) The angle φ was defined using the centers of mass (COM) of P63-E66 (blue), P47-A50, and L51-G54 (green). (FIG. 1E) The change of angle φ (red) versus the simulation time compared with the angle between the alpha helix (colored dark grey in 1D) and the X-Y plane. (FIG. 1F) The free energy landscape along the reaction coordinate when GSH is present (black) and absent (dark grey).

FIGS. 2D-2F). Key residues are shown in stick model and polar interactions are showed in black dashed lines.

(FIG. 3A) R38 will adopt different conformation during the cap opening process. (FIG. 3B) Dose-dependent inhibition of lapatinib against mPGES-1. (FIG. 3C) Simulated binding conformation of lapatinib against mPGES-1. The cap domain is colored in grey and some key residues interacting with lapatinib are showed in sticks. Hydrogen bonds are showed in black dashed lines. (FIG. 3D) Inhibition of mPGES-1 with lapatinib at constant 1 μM concentration and GSH at different concentrations, indicating lapatinib (indicated as C8 in panel D) is a GSH-competitive inhibitor.

(FIG. 4A) Arthralgia (pain in joint) (FIG. 4B) Musculoskeletal pain (FIG. 4C) Headache (FIG. 4D) Oral pain. Data was collected from clinical trials showed in Table 7. p values were calculated based on $\chi^2$ tests.

(FIG. 5A) Arthralgia (pain in joint). (FIG. 5B) Bone pain. (FIG. 5C) Pain in extremity (limb). (FIG. 5D) Musculoskeletal pain. (FIG. 5E) Back pain. (FIG. 5F) Headache. Group I: oral lapatinib 1000 mg daily with trastuzumab (8 mg/kg IV loading dose, followed by 6 mg/kg IV every 3 week) for 52 weeks; Group II: weekly trastuzumab for 12 weeks (4 mg/kg IV loading dose, followed by 2 mg/kg IV weekly), followed by a 6-week washout period, followed by oral lap 1500 mg daily for 34 weeks. Group III: oral lapatinib 1500 mg daily for 52 weeks. Control group: trastuzumab 8 mg/kg IV, followed by 6 mg/kg IV every 3 weeks for 52 weeks.

DESCRIPTION OF EXEMPLARY EMBODIMENTS

Figure 2A:
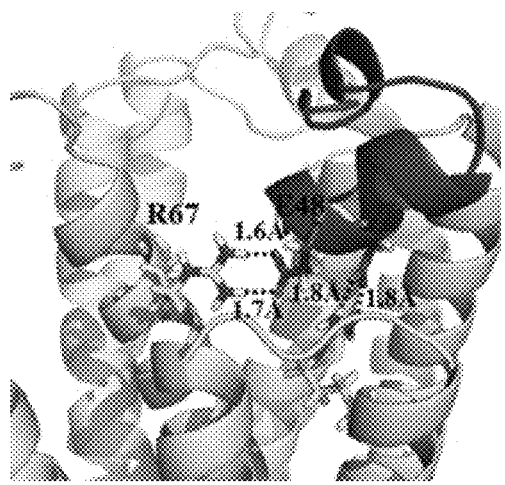
FIGS. 2A-2F. Detailed interactions between residues of the cap domain of mPGES-1 in the closed conformation observed from different orientations (FIGS. 2A, 2B, and 2C) and the open conformation observed from the corresponding orientations (FIGS. 2D, 2E, and 2F, respectively). Protein is showed in grey cartoon and the cap domain is showed in black (closed conformation in FIGS. 2A-2C) or dark grey (open conformation.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Lapatinib, methods of production, and methods of use in connection with treatment of cancer are described, for example, in U.S. Pat. Nos. 6,713,485, 6,727,256, 7,157,466, 8,513,262, and 8,821,927. Lapatinib is known to be a Protein Kinase Inhibitor, which reversibly blocks phosphorylation of the epidermal growth factor receptor (EGFR) and ErbB2, which have been identified in connection with the growth of various tumor types. Lapatinib has been approved by the Food and Drug Administration for use in treating breast cancer and is used in doses of 1250-1500 mg/day in combination with capecitabine.

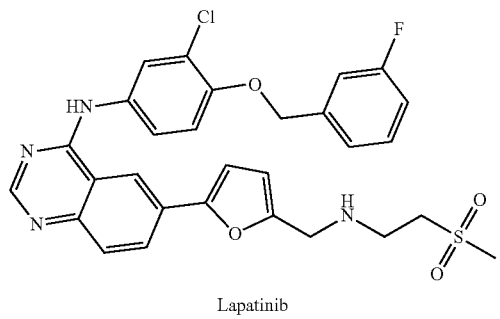 [SMILES: CS(=O)(=O)CCNCc1ccc(-c2ccc3ncnc(Nc4ccc(OCc5cccc(F)c5)c(Cl)c4)c3c2)o1]

Lapatinib

As disclosed herein, the present inventors have identified lapatinib to be a potent mPGES-1 inhibitor, with an $IC_{50}$ of about 800 nM. Accordingly, and as described herein in greater detail, the presently-disclosed subject matter includes methods of using Lapatinib to inhibit mPGES-1 and methods of using Lapatinib to treat pain.

In some embodiments, the method for treating pain involves administering an effective amount of lapatinib or a pharmaceutically-acceptable salt thereof to a subject in need of treatment for pain. In some embodiments, the method also involves a step of identifying the subject has having a need for analgesia or treatment for pain.

In some embodiments, the method of inhibiting mPGES-1 in a subject involves administering an effective amount of lapatinib or a pharmaceutically-acceptable salt thereof to the subject, thereby inhibiting mPGES-1.

The terms "treatment" or "treating" refer to the medical management of a subject with the intent to cure, ameliorate, reduce, or prevent pain. As will be recognized by one of ordinary skill in the art, the term "cure" does not refer to the ability to completely remove all pain in all cases. For example, in some embodiments, a cure can refer to a decrease in pain at a level of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. Similarly, as will be recognized by one of ordinary skill in the art, the term "prevent" does not refer to an ability to completely remove any and all onset of pain.

Likewise, as will be recognized by one of ordinary skill in the art, the term "inhibiting" or "inhibition" does not refer to the ability to completely inactivate all target biological activity in all cases. Rather, the skilled artisan will understand that the term "inhibiting" refers to decreasing biological activity of a target, such as a prostaglandin E synthase, such as can occur with a ligand binding site of the target is blocked, or when a non-native complex with the target is formed. Such decrease in biological activity can be determined relative to a control, wherein an inhibitor is not administered and/or placed in contact with the target. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. The term "inhibitor" refers to a compound of composition that inactivates or decreases the biological activity of a target, such as a prostaglandin E synthase.

The terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In some embodiments of the methods disclosed herein, the subject and/or patient does not have cancer.

The term "administering" refers to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-thbenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In some embodiments of the presently disclosed subject matter, lapatinib is provided or administered at a dose of from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 275 mg, from about 275 mg to about 300 mg, from about 300 mg to about 325 mg, from about 325 mg to about 350 mg, from about 350 mg to about 375 mg, from about 375 mg to about 400 mg, from about 400 mg to about 425 mg, from about 425 mg to about 450 mg, from about 450 mg to about 475 mg, from about 475 mg to about 500 mg, from about 500 mg to about 525 mg, from about 525 mg to about 550 mg, from about 550 mg, from about 575 mg, from about 575 mg to about 600 mg, from about 600 mg to about 625 mg, from about 625 mg to about 650 mg, from about 650 mg to about 675 mg, from about 675 mg to about 700 mg, from about 700 mg to about 725 mg, from about 725 mg to about 750 mg, from about 750 mg to about 775 mg, from about 775 mg to about 800 mg, from about 800 mg to about 825 mg, from about 825 mg to about 850 mg, from about 850 mg to about 875 mg, from about 875 mg to about 900 mg, from about 900 mg to about 925 mg, from about 925 mg to about 950 mg, from about 950 mg to about 975 mg, from about 1000 mg to about 1025 mg, from about 1025 mg to about 1050 mg, from about 1050 mg to about 1075 mg, from about 1075 mg to about 1100 mg, from about 1100 mg to about 1125 mg, from about 1125 mg to about 1150 mg, from about 1150 mg to about 1175 mg, from about 1175 mg to about 1200 mg, from about 1200 mg to about 1225 mg, from about 1225 mg to about 1250 mg, from about 1250 mg to about 1275 mg, from about 1275 mg to about 1300 mg, from about 1300 mg to about 1325 mg, from about 1325 mg to about 1350 mg, from about 1350 mg to about 1375 mg, from about 1375 mg to about 1400 mg, 1400 mg to about 1425 mg, from about 1425 mg to about 1450 mg, from about 1450 mg to about 1475 mg, or from about 1475 mg to about 1500 mg.

In some embodiments of the presently disclosed subject matter, lapatinib is provided or administered at a dose of from about 50 mg to about 1500 mg. In some embodiments, the lapatinib is provided or administered at a dose of about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, or 1500 mg.

In some embodiments of the methods disclosed herein, lapatinib can be used to treat various types of pain. For example, the methods can be used to treat chronic or acute pain. In some embodiments the methods can be used to treat arthralgia (pain in joint), bone pain, pain in an extremity (limb), musculoskeletal pain, myalgia, and headache.

In some embodiments of the methods disclosed herein, opioids are contraindicated for the subject. Information about opioid contraindications can be found, for example, in Cohen, Brandon, and William G. Gossman. *Opioid, Analgesics*, Oct. 6, 2017, and *VA/DoD Clinical Practice Guidelines for Management of Opioid Therapy for Chronic Pain*, Version 3.0 (2017), both of which are incorporated herein by this reference.

For example, in some embodiments the subject has or is associated with one or more of the following conditions: history of or a current substance use disorder, history of or a current alcohol addiction, history of or a current opioid addiction or opioid use disorder (OUD), suspected opioid misuse (e.g., overdose, early refills, diversion, taking more than prescribed).

For another example, in some embodiments the subject has or is associated with one or more of the following conditions: prior diversion of controlled substances (providing the medication to someone for whom it was not intended), a family history of substance abuse, a history of legal problems, a history of incarceration, frequent contact with high-risk individuals or environments, social instability, multiple psychosocial stressors, history of previous problems with employers, family, and friends, history of risk-taking and thrill-seeking behavior, and history of childhood abuse.

For another example, in some embodiments the subject has or is associated with one or more of the following conditions: history of or current mental health disorders, acute psychiatric instability risk for suicide, depression, personality disorders, posttraumatic stress disorder, sleep disorders, unstable psychiatric disorder, and anxiety.

For another example, in some embodiments the subject has or is associated with one or more of the following conditions: young age (e.g., below 30, below 21, below 18), history of seizure disorder, cardiac condition, long QT syndrome or QT prolongation, chronic pulmonary disease (COPD), severe respiratory instability, comatose patients, phaeochromocytoma, centralized pain conditions such as fibromyalgia, chronic obstructive pulmonary disease, cognitive impairment or otherwise having an inability to manage opioid therapy responsibly, traumatic brain injury, gastrointestinal (GI) motility problems (e.g., toxic megacolon, GI pain syndromes, narcotic bowel syndrome, irritable bowel syndrome), immune status changes, hepatic, renal, or pulmonary disease, osteoporosis, obstructive sleep apnea, central sleep apnea, mild-moderate asthma, known or suspected paralytic ileus, and receiving treatment using medical marijuana.

For another example, in some embodiments the subject is taking a drug capable of inducing life-limiting drug-drug interaction with opioids. In some embodiments the subject is receiving a monoamine oxidase inhibitor (MAOI), propoxyphene, or a central nervous system depressant. For another example, in some embodiments the subject has an allergy or sensitivity to opioids.

In some embodiments of the methods disclosed herein, NSAIDs are contraindicated for the subject.

For example, in some embodiments the subject has or is associated with one or more of the following conditions: cardiovascular disease, cerebrovascular disease, myocardial infarction, transient ischemic attack, stroke, coronary artery disease, coronary artery bypass surgery, congestive heart failure, and history thereof or risk thereof.

For another example, in some embodiments the subject has or is associated with one or more of the following conditions: peptic ulcer or stomach bleeding, uncontrolled hypertension, kidney disease, Irritable bowel syndrome, inflammatory bowel disease, Crohn's disease, ulcerative colitis, a prior gastric bypass surgery, a family history of gastrointestinal (GI) problems.

For another example, in some embodiments the subject is pregnant. In some embodiments, the subject is in the third trimester of pregnancy.

For another example, in some embodiments the subject has an allergy or sensitivity to nonsteroidal anti-inflammatory drugs (NSAIDs).

The presently-disclosed subject matter further includes pharmaceutical compositions comprising lapatinib or a pharmaceutically-acceptable salt. In some embodiments, the method of inhibiting mPGES-1 in a subject involves administering an effective amount of a pharmaceutical composition comprising lapatinib or a pharmaceutically-acceptable salt thereof to the subject, thereby inhibiting mPGES-1. In some embodiments, the method for treating pain involves administering an effective amount of a pharmaceutical composition comprising lapatinib or a pharmaceutically-acceptable salt thereof to a subject in need of treatment for pain. In some embodiments, the method also involves a step of identifying the subject has having a need for analgesia or treatment for pain.

Pharmaceutical compositions, as disclosed herein, include lapatinib and further include a pharmaceutically-acceptable carrier. In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compound can be formulated with suitable polymeric or hydrophobic materials (e.g., as an emulsion in an acceptable oil) or ion exchange resins, or as sparingly soluble derivatives (e.g., as a sparingly soluble salt).

The compound can also be formulated in rectal compositions (e.g., suppositories or retention enemas containing conventional suppository bases such as cocoa butter or other glycerides), creams or lotions, or transdermal patches.

The compound has utility as a PGES inhibitor, and in particular, mPGES-1. In this regard, the compounds and pharmaceutical compositions of the presently disclosed subject matter have anti-inflammatory utilities. In this regard, in some embodiments, the pharmaceutical compositions of the presently-disclosed subject matter further include a second compound having PGES inhibition activity, having anti-inflammatory activity, being useful for treatment of an inflammation disorder, and/or being useful for treatment of symptoms associated inflammation and/or an inflammation disorder.

Exemplary conditions in which treatment for inflammation and/or treatment for pain are useful can include, for example, menstrual cramps (dysmenorrhea), lupus and skin disorders such as psoriasis and actinic keratosis. Additional exemplary conditions include, but are not limited to, actinomycosis, bacterial pneumonia, brucellosis, bubonic plague, buruli ulcer, campylobacteriosis, cat-scratch disease, chancroid, chlamydia, *Clostridium difficile* infection, diphtheria, ehrlichiosis, epidemic typhus, erysipelas, glanders, granuloma inguinale, group A streptococcal infection, impetigo, Lemierre's syndrome, legionellosis (legionnaires disease), leprosy, leptospirosis, listeriosis, lyme disease, melioidosis, meningitis, meningococcal disease, necrotizing fasciitis, osteomyelitis, paratyphoid fever, plague, pneumonic plague, psittacosis, Q fever, rat-bite fever, relapsing fever, rheumatic fever, Rocky Mountain spotted fever, salmonellosis, scarlet fever, sepsis, shigellosis, staphylococcal scalded skin syndrome, syphilis, tetanus, tularemia, typhoid fever, vibriosis (*Vibrio*), whooping cough, yersiniosis, babesiosis, chikungunya virus infection (chikungunya), Dengue, 1, 2, 3, 4 (Dengue Fever), encephalitis, enterovirus infection, granuloma inguinale, haemophilus influenza disease, Type B (Hib or H-flu), hantavirus pulmonary syndrome (HPS), hepatitis A (Hep A), hepatitis B (Hep B), hepatitis C (Hep C), hepatitis D (Hep D), hepatitis E (Hep E), herpes, histoplasmosis infection (Histoplasmosis), human papillomavirus (HPV), influenza (Flu), malaria, measles, meningitis, viral meningitis, middle east respiratory syndrome coronavirus (MERS-CoV), mumps, norovirus, powassan, rubella, scabies, severe acute respiratory syndrome (SARS), varicella (Chickenpox), west nile virus, yellow fever, zika virus infection (Zika), ankylosing spondylitis, anti-GBM/anti-TBM nephritis, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticarial, chagas disease, chronic inflammatory demyelinating polyneuropathy (CIDP), Crohn's disease, dermatomyositis, discoid lupus, endometriosis, eosinophilic esophagitis (EoE), eosinophilic fasciitis, fibromyalgia, fibrosing alveolitis, giant cell arteritis (temporal arteritis), giant cell myocarditis, glomerulonephritis, granulomatosis with polyangiitis, herpes gestationis or pemphigoid gestationis (PG), inclusion body myositis (IBM), juvenile arthritis, juvenile diabetes (Type 1 diabetes), juvenile myositis (JM), kawasaki disease, leukocytoclastic vasculitis, lupus, microscopic polyangiitis (MPA), myositis, neonatal lupus, palindromic rheumatism (PR), pars planitis (peripheral uveitis), perivenous encephalomyelitis, polymyalgia rheumatic, polymyositis, primary sclerosing cholangitis, progesterone dermatitis, psoriasis, psoriatic arthritis, teactive arthritis, relapsing polychondritis, rheumatic fever, rheumatoid arthritis, sarcoidosis, scleritis, subacute bacterial endocarditis (SBE), Takayasu's arteritis, temporal arteritis/giant cell arteritis, transverse myelitis, type 1 diabetes, ulcerative colitis (UC), uveitis, and vasculitis.

The presently-disclosed subject matter further includes kits. In some embodiments, a kit can include a compound or pharmaceutical composition as described herein, packaged together with a second compound, composition, or treatment device having PGES inhibition activity, having anti-inflammatory activity, being useful for treatment of an inflammation disorder, and/or being useful for treatment of pain.

In some embodiments, a kit can include a compound or pharmaceutical composition as described herein, packaged together with a device useful for administration of the compound or composition. As will be recognized by those or ordinary skill in the art, the appropriate administration aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The presently-disclosed subject matter further includes methods of inhibiting mPGES. In some embodiments, the method can include contacting the compound or composition described herein with mPGES-1, thereby forming a complex with the compound and mPGES-1. In some embodiments, the method can include administering an effective amount of a compound or pharmaceutical composition, as described herein.

The presently-disclosed subject matter also includes a unique strategy for identifying FDA-approved drugs suitable for use as effective analgesics. The system for identifying suitable for use as effective analgesics is referred to herein as "DREAM-in-CDM" (Drug Repurposing Effort Applying Integrated Modeling-in vitro/vivo-Clinical Data Mining). The DREAM-in-CDM approach consists of three steps: (1) computational modeling to predict which FDA-approved drugs may favorably bind with the desirable drug target (mPGES-1 in this project); (2) in vitro and/or in vivo assays to validate the computational predictions; (3) clinical data mining to confirm the efficacy associated with the required clinical end points for the new therapeutic indication. By using the DREAM-in-CDM approach, the present-inventors identified lapatinib as a human mPGES-1 inhibitor which can be used to significantly relief various types of pain.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

The terms "about," "up to," "generally," and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

As a prominent target for new anti-inflammatory drugs, mPGES-1 (microsomal prostaglandin E synthase-1) has been extensively studied and various inhibitors have been reported. However, very few inhibitors could enter clinical trials and none has been approved by FDA. Meanwhile, the detailed catalytic mechanism of mPGES-1 never got an convincible explanation. In the in silico part of the studies described in these Examples, the process of how mPGES-1 adopts an alternative conformation to control the access of co-factor GSH (glutathione) and its impact on its function were observed. Based on the simulation result, an explanation for the difference between the X-ray and CryoEM (cryogenic electron microscope) structure of mPGES-1 was disclosed. Additionally, the FDA approved drug, lapatinib, was identified as a mPGES-1 inhibitor by virtual screening and in vitro experiments. By mining on the available clinical trial data, solid evidence was found that lapatinib can be used to relieve various types of pain in cancer patients. Since lapatinib has been established as being very well tolerated, lapatinib can be repurposed as a new treatment for pain.

Results

Predictions from computational modeling. As is well known, it is usually difficult to obtain a crystal structure of a membrane protein like mPGES-1. In 2013, Sjogren et. al.[58] reported a high-resolution structure of mPGES-1, which showed significant structural difference to the earlier CryoEM structure reported in 2011. In 2014, the first co-crystal structure (PDB ID: 4BPM)[59] with an inhibitor bound was reported. Based on the new X-ray crystal structure, the present inventors wanted to understand why the inhibitors show less than expected activities in vivo by carrying out computational modeling.

Since there are major differences between the CryoEM and X-ray crystal structures, it has been suggested that mPGES-1 might adopt a different conformation to function in solution.[58] Starting from the new X-ray crystal structure of 4AL0 with a remarkably high resolution at 1.2 Å, the protein structure of mPGES-1 was modeled together with its co-factor glutathione (GSH) in the presence of a phospholipid bilayer (DOPC) and a water box by using the CHARMM-GUI Membrane Builder software,[60] and then carried out a long MD simulation (100 ns) using the NAMD program.[61] Throughout the 100 ns MD simulation, the average root-mean-square deviation (RMSD) was only at 1.9 Å (FIG. 1A), the protein structure was very stable. The anticipated conformational change of mPGES-1 was not observed during the MD simulation.

To examine whether GSH could induce a conformational change, another MD simulation was performed on mPGES-1 in the absence of GSH, but with the same phospholipid bilayer and water box. In this simulation, the protein appeared to be much less stable, with an average RMSD of 2.8 Å (FIG. 1A). In particular, a small portion (F44 to D62) of the protein had a major conformational change, while the remaining protein structure was still very stable (FIG. 1B). The flexible residues (from F44 to D62, FIG. 1C) are located right on the GSH binding site. In the presence of GSH, this domain acts like a cap of the GSH-binding site, preventing GSH from contacting the solvent. When the cap domain adopts this completely different "open" conformation, the catalytic site will be able to gain direct access to cytoplasm, allowing GSH to freely enter or leave the site.

Figure 2B:
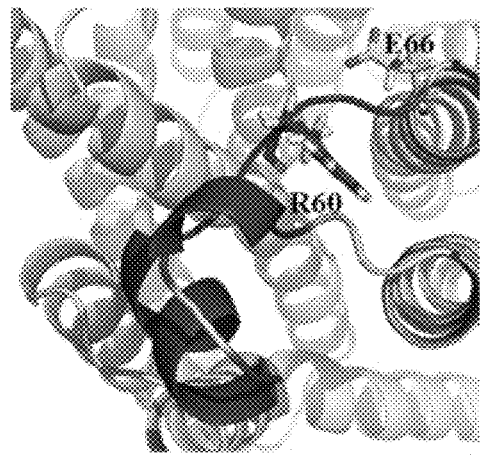
Figure 2C:
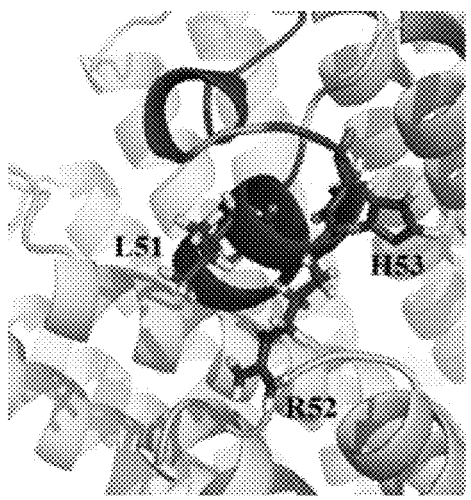
Figure 2D:
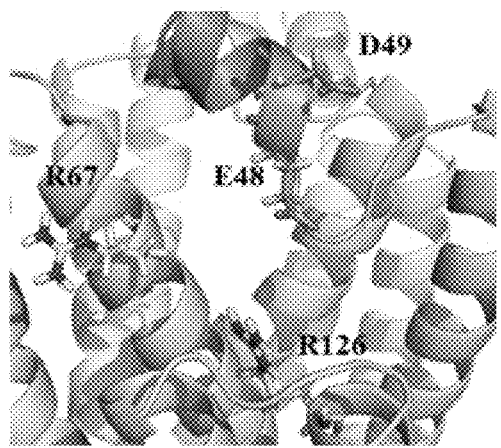
Figure 2E:
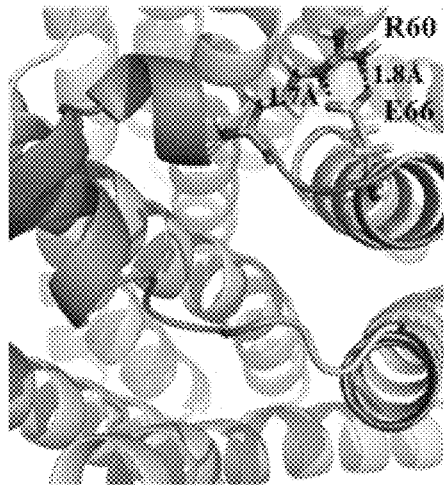
Figure 2F:
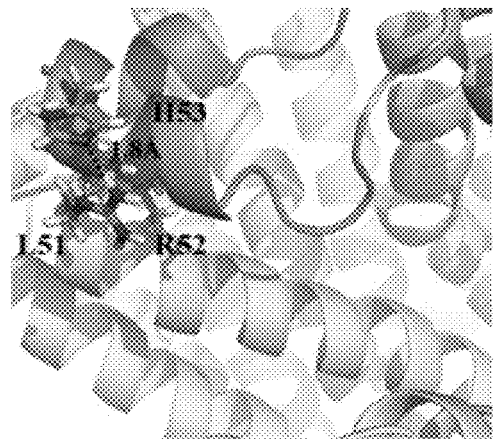

The major structural difference between the open and closed conformations in the cap domain are shown in FIG. 2 and summarized in Table 1. In the simulated open conformation, despite the conformational change and loss of a few polar interactions, new polar interactions are formed at the same time to compensate the loss. Thus, the open conformation is expected to be at least as stable as the closed conformation in solution.

TABLE 1

Comparison between the open and closed conformations in the main interactions of amino-acid residues in the cap domain.

| Residue | Closed conformation | Open conformation |
|---|---|---|
| E48 | Salt bridge with R67 | Side chain exposed in water |
| D49 | Salt bridge with R126 | Hydrogen bond with N46 |
| L51 | Side chain exposed in water | Side chain buried |
| R52 | Side chain exposed in water | Hydrogen bond with Side chain of H53 |
| H53 | Side chain exposed in water | Hydrogen bond with Side chain of R52 |
| Q57 | Stab into water | Hydrogen bond with S61 |
| R60 | Hydrogen bond with backbone oxygen of K41 | Salt bridge with E66 |
| E66 | Side chain exposed in water | Salt bridge with R60 |

In order to know the energetics of this significant conformational change, a potential of mean force (PMF) study was performed on the mPGES-1 structure using the umbrella sampling method. To perform this PMF study, a reaction coordinate must be defined for the PMF simulation. Since the main part of this cap domain is an α-helix, the angle between the vector of this α-helix and the X-Y plane was used as the reaction coordinate. However, due to the technical restriction of the MD simulation software, the X-Y plane cannot be chosen as an anchor point, thus, the COM (center of mass) of P63-E66 was chosen as the anchor point because it is stable during the simulation (FIG. 1D). The COM(P63-E66)-COM(P47-A50)-COM(L51-G54) angle is highly correlated with the abovementioned angle between the α-helix and the X-Y plane (FIG. 1E), indicating that it is reasonable to use this angle as the reaction coordinate.

The WHAM[62] program was then used to analyze relative free energy differences along the reaction coordinate. The results are shown in FIG. 1F, revealing two local minima: one associated with the closed conformation, and the other with the open conformation. The free energy difference between these two local minima is about 0.5 kcal/mol and the energy barrier is only 2.5 kcal/mol, which means that these two conformations can easily change from one to another in solution. Further, a targeted MD (TMD) simulation was also performed, followed by the similar PMF simulation on the mPGES-1 in the absence of GSH. The obtained energetic data are also depicted in FIG. 1F, showing that, in the presence of GSH, the closed conformation has a much lower free energy than the open conformation. Based on the energetic data in FIG. 1F, the free mPGES-1 protein (without GSH) should mainly, but not exclusively, exist in the open conformation, whereas the protein with GSH bound should exclusively exist in the closed conformation. These results explain why the open conformation can be observed only in the absence of GSH.

The computationally-determined open conformation of mPGES-1 was used further for virtual screening of FDA-approved drugs for their potential binding with the open conformation of mPGES-1. The virtual screening was performed by using a multiple-step computational screening protocol.[16] It was the hope that an inhibitor targeting the open conformation of mPGES-1 might be able to overcome the problems of the currently known mPGES-1 inhibitors. Based on the virtual screening, the following 18 FDA-approved drugs were predicted to be inhibitors of mPGES-1.

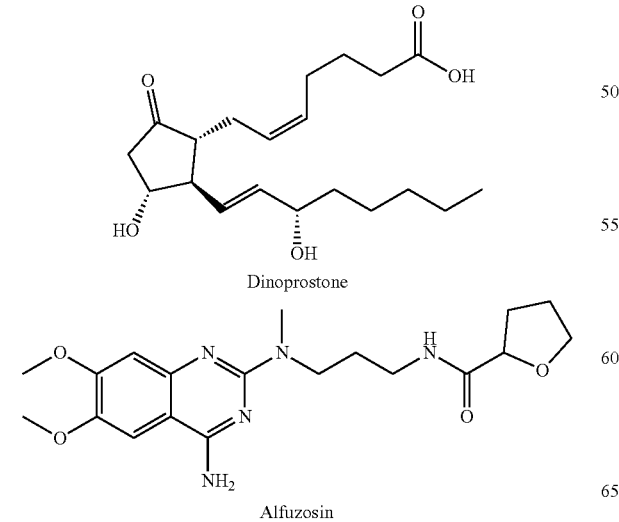

Dinoprostone

Alfuzosin

Acitretin

Dipyridamole

Doxazosin

Lapatinib

Calcipotriene

-continued
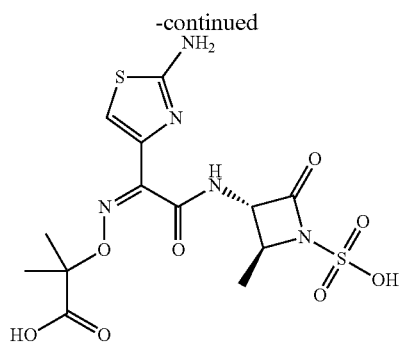
Aztreonam
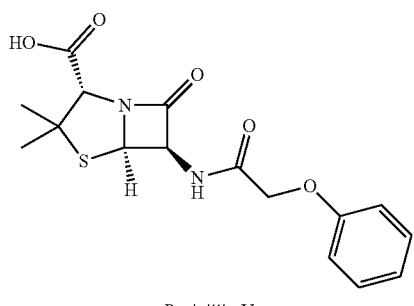
Penicillin V
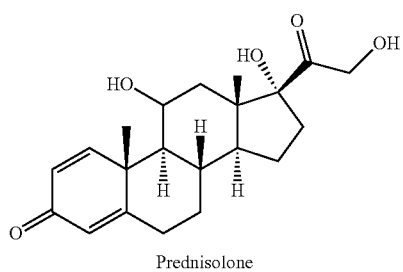
Prednisolone
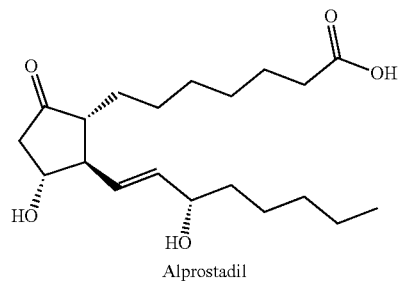
Alprostadil
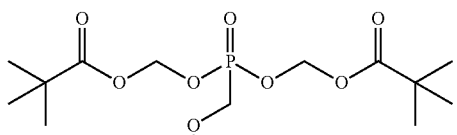
Adefovir Dipivoxil
-continued
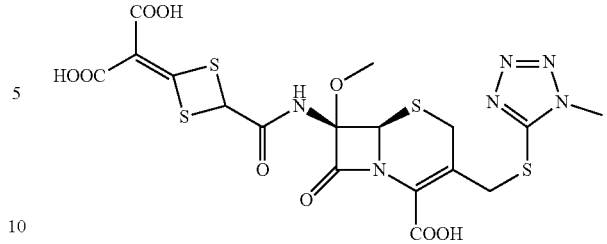
Cefotetan
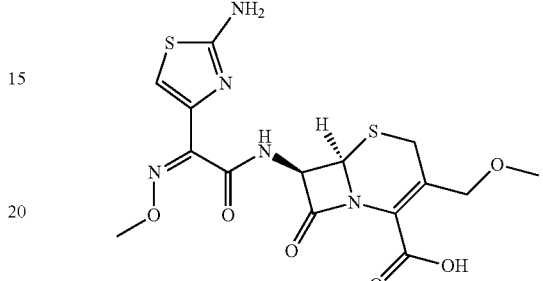
Cefpodoxime
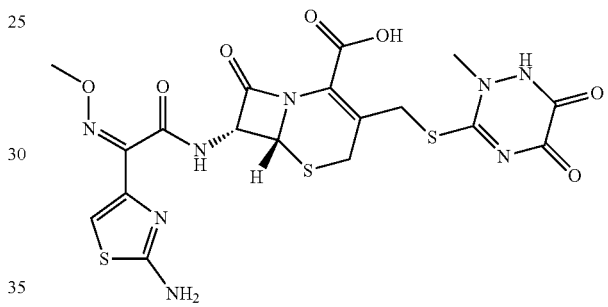
Ceftriaxone
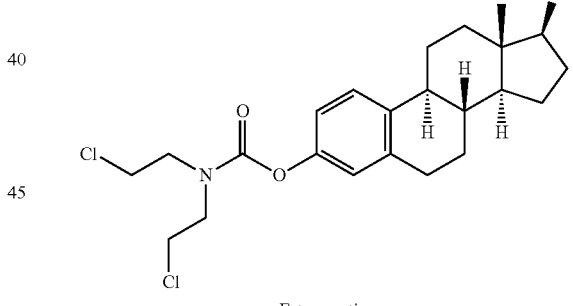
Estramustine
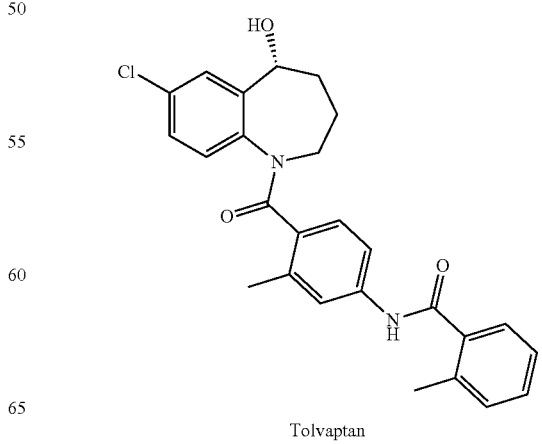
Tolvaptan

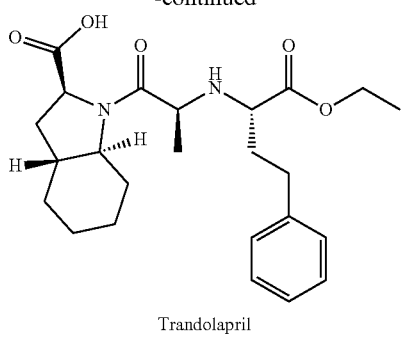

Trandolapril

Data Obtained from In Vitro Activity Assays.

The above computational predictions were followed by in vitro activity assays for their actual inhibitory activity against human mPGES-1 using an ELISA assay previously-described.[16-17, 19] Specifically, a total of 18 FDA-approved drugs were assayed for their inhibitory activity against human mPGES-1. According to the initial single-concentration (at 10 μM) screening, the 18 drugs inhibited the mPGES-1 activity by 4% to 99%, and 10 out of the 18 drugs at a 10 μM inhibited the mPGES-1 activity by at 44% or more. The top-10 drugs were assayed further for their $IC_{50}$ values (see Table 2), with lapatinib being the most potent one ($IC_{50}$=0.8 μM or 800 nM). In addition, some other FDA-approved drugs can also significantly inhibit human mPGES-1, but with relatively higher $IC_{50}$ values. Accordingly, lapatinib was focused upon in further experimental tests in this investigation.

TABLE 2

The FDA-approved compounds selected from virtual screening and tested for their in vitro inhibitory activity against human mPGES-1.

| Compound Name | Inhibition (%) at 10 μM | $IC_{50}$ (μM) |
|---|---|---|
| Dinoprostone | 4 | |
| Alfuzosin | 22 | |
| Acitretin | 83 | 3.5 ± 1.6 |
| Dipyridamole | 36 | |
| Doxazosin | 21 | |
| Lapatinib Ditosylate | 99 | 0.8 ± 0.1 |
| Calcipotriene | 68 | 3.0 ± 1.1 |
| Aztreonam | 53 | 11.4 ± 1.1 |
| Penicillin V Potassium | 36 | |
| Prednisolone | 44 | 12.6 ± 1.6 |
| Alprostadil | 11 | |
| Adefovir Dipivoxil | 19 | |
| Cefotetan Disodium | 44 | 13.5 ± 4.0 |
| Cefpodoxime Proxetil | 47 | 29.7 ± 6.3 |
| Ceftriaxone | 57 | 7.2 ± 2.4 |
| Estramustine Phosphate | 36 | |
| Tolvaptan | 52 | 10.2 ± 2.5 |
| Trandolapril | 54 | 9.0 ± 2.3 |

Figure 3A:
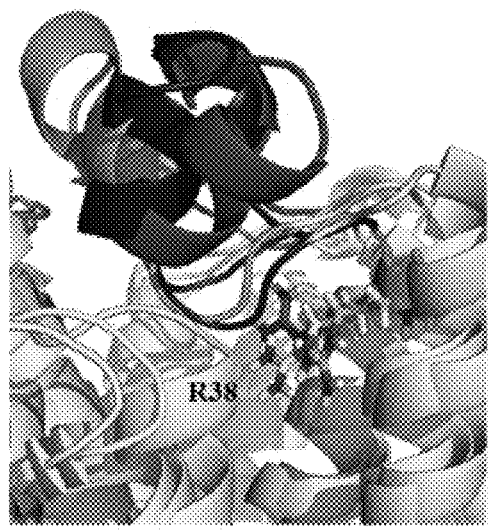
FIG. 3A-3D.
Figure 3B:
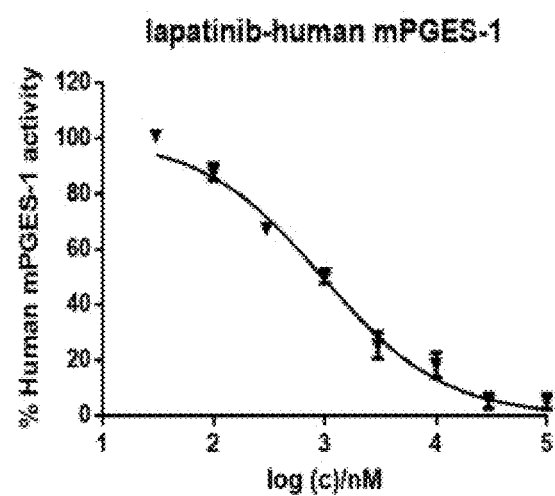
Figure 3C:
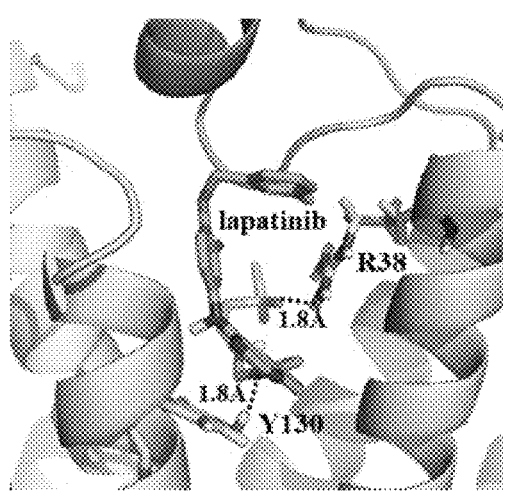
Figure 3D:
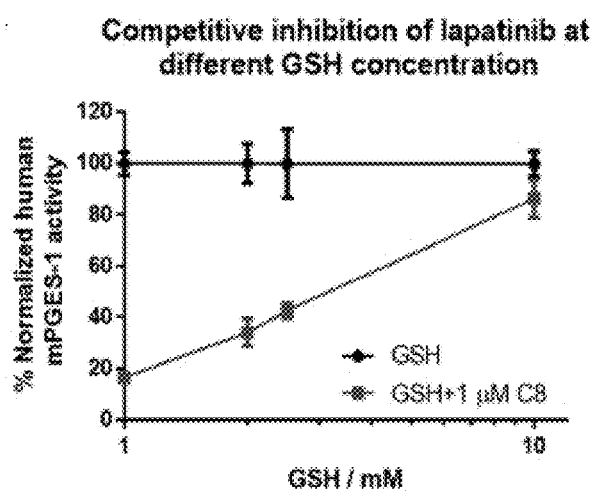

Depicted in FIG. 3 are the computationally modeled protein-ligand binding structures and in vitro activity data obtained for lapatinib. In particular, as seen in FIG. 3D, lapatinib indeed competes with co-factor GSH, which is consistent with the modeled binding mode in which lapatinib occupies the GSH-binding site.

Clinical Data Mining.

As an FDA-approved drug, lapatinib was tested in many clinical trials. In clinical data mining, the first question was whether lapatinib can reach the effective in vivo concentration in human body comparable to the $IC_{50}$ value (~800 nM). To address this question, the pharmacokinetic data was collected, particularly $C_{max}$ values, of lapatinib from five different clinical trials and estimated the corresponding $C_{max}$ values in different organs. According to the data collected in Table 3, the plasma $C_{max}$ of lapatinib in its usual dosage forms should be well above its $IC_{50}$ against mPGES-1. In addition, the reported ratios of $C_{max}$ values in various organs of rat to $C_{max}$ in rat plasma, along with the $C_{max}$ values in human plasma, were used to predict the $C_{max}$ values in the corresponding organs of human corresponding to the $C_{max}$ values in human plasma. The predicted $C_{max}$ values in various human organs are also listed in Table 3. As seen in Table 3, lapatinib may have much higher concentrations in various human organs compared to the corresponding concentration in human plasma. In particular, $C_{max}$ is predicted to be as high as ~2 μM (>$IC_{50}$) in lung and ~1.3 μM (>$IC_{50}$) in kidney at a dose of only 50 mg. Notably, kidney is rich of mPGES-1.[19]

TABLE 3

$C_{max}$ (μM) of lapatinib in human plasma from clinical pharmacokinetic data and the predicted $C_{max}$ (μM) in various human organs associated with various doses.

| | $C_{max}$ (μM) | Predicted $C_{max}$ (μM) in various organs[e] | | | | | |
|---|---|---|---|---|---|---|---|
| Dose | in plasma | Brain | Heart | Lung | Kidney | Intestine | Liver |
| 10 mg | 0.019[a] | 0.002 | 0.041 | 0.311 | 0.201 | 0.100 | 0.002 |
| 25 mg | 0.040[a] | 0.004 | 0.085 | 0.649 | 0.420 | 0.210 | 0.005 |
| 50 mg | 0.124[a] | 0.012 | 0.267 | 2.037 | 1.319 | 0.658 | 0.015 |
| 100 mg | 0.213[a] | 0.021 | 0.458 | 3.500 | 2.266 | 1.131 | 0.026 |
| 175 mg | 0.380[a] | 0.038 | 0.817 | 6.243 | 4.043 | 2.018 | 0.046 |
| 250 mg | 0.546[a] | 0.055 | 1.174 | 8.971 | 5.809 | 2.899 | 0.066 |
| 500 mg | 1.756[b] | 0.176 | 3.775 | 28.851 | 18.684 | 9.324 | 0.211 |
| 650 mg | 2.238[b] | 0.224 | 4.812 | 36.770 | 23.812 | 11.884 | 0.269 |
| 900 mg | 2.926[b] | 0.293 | 6.291 | 48.074 | 31.133 | 15.537 | 0.351 |
| 1000 mg | 3.184[b] | 0.318 | 6.846 | 52.313 | 33.878 | 16.907 | 0.382 |
| 1250 mg | 6.060[c] | 0.606 | 13.029 | 99.566 | 64.478 | 32.179 | 0.727 |
| 1500 mg | 8.598[d] | 0.860 | 18.486 | 141.265 | 91.483 | 45.655 | 1.032 |

[a]Data in the row come from clinical trial by Bence et al.[63] GW572016 ditosylate monohydrate formulated in oral suspension;

[b]Data in the row come from clinical trial EGF10004, Lapatinib (GlaxoSmithKline, Research Triangle Park, NC) was supplied as 100-mg and 250-mg tablets for daily oral administration;

[c]Data in this row come from clinical trial NCT00477464. Lapatinib was orally administered at 1250 mg once daily;

[d]Data in the row come from clinical trial NCT00486954 and NCT01138046, 36 data points from 6 subgroups were combined for the average $C_{max}$. Lapatinib was in 6 pills at 250 mg each once oral daily;

[e]All of the predicted $C_{max}$ values are calculated based on the ratios of the drug concentrations in various organs to that in plasma in rats reported in literature.[64]

In 2010, Kaufman et al. conducted a phase II clinical trial (NCT00105950) with a focus on the quality of life accounting for many parameters including pain symptoms in inflammatory breast cancer patients who used lapatinib, and they concluded that lapatinib monotherapy may "provide relief from symptoms, including pain, in the short term".[65] However, their sample size was too small (n=17 for the lapatinib group). Thus, their data was not statistically significant (p>0.05) in terms of the pain-relieving effects of lapatinib.

Figure 4A:
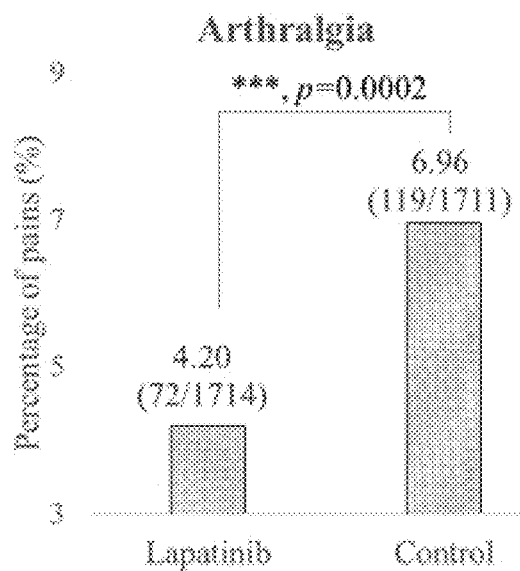
FIG. 4A-4D. Number and percentage of patients complained about various pains used lapatinib compared with control drugs or placebo in clinical trials.
Figure 4B:
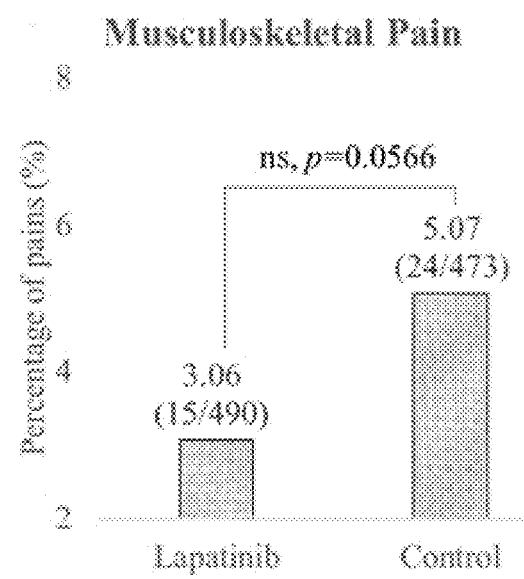
Figure 4C:
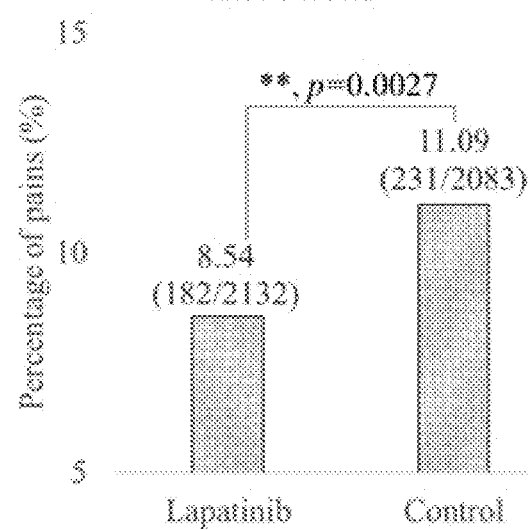
Figure 4D:
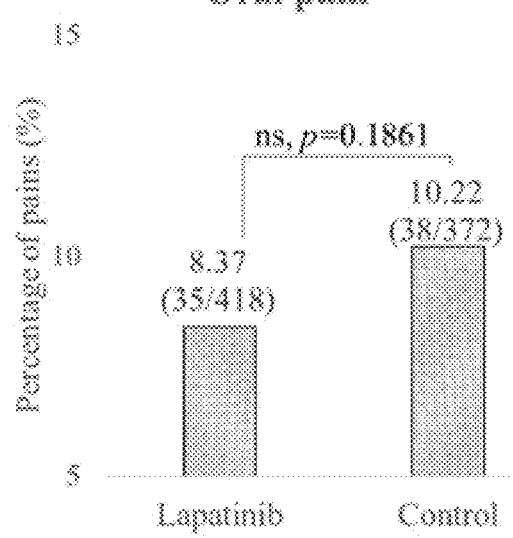

Examining all available data from clinical trials, most of the Phases II and III clinical trials used lapatinib at the doses ranging from 1000 mg to 1500 mg per day. Under these dose conditions, lapatinib expected to show analgesic effects in these trials according to the $C_{max}$ values listed in Table 3. First, clinical trial NCT00374322[66] was considered, including women with early-stage ErbB2-overexpressing breast cancer who had not been previously treated with trastuzumab. The "other adverse events" part of the clinical report was analyzed. While in the lapatinib group (n=1573) there were more patients complaining about diarrhea and rash compared to the placebo group (n=1574), there were less patients reporting headache (140/1573 vs 185/1574) and arthralgia (69/1573 vs 113/1574) compared to the placebo group. These differences are also statistically significant (p=0.0016 and p=0.0004, respectively), according to the statistical analysis ($\chi^2$ tests; see FIG. 4).

Since there have been multiple lapatinib clinical trials, it might be interesting to collect all of the available data associated with the comparable dose conditions together for examining the efficacy of lapatinib as an analgesic (a new therapeutic indication which has never been considered for lapatinib). In particular, all of the data from clinical trials NCT00424255, NCT00390455, NCT00371566, and NCT00374322 was collected together as a larger dataset. In these clinical trials, they used the same dose of lapatinib but recruited different populations of patients (with different types of cancer). According to the $\chi^2$ test, the difference between the combined dataset and any individual trial dataset (e.g. NCT00374322) was insignificant (p>0.05). Hence, it is reasonable to analyze the analgesic effects of lapatinib using the combined dataset. The combined clinical data revealed that, for several types of pain, there were significantly fewer patients complaining pain compared to the control group in which the patients given either placebo or other drugs (see Table 4).

TABLE 4

Number and percentage of patients complaining about various pains after using afatinib (EGFR and HER2 dual inhibitor) compared to the placebo in Phase III clinical trial NCT00656136.

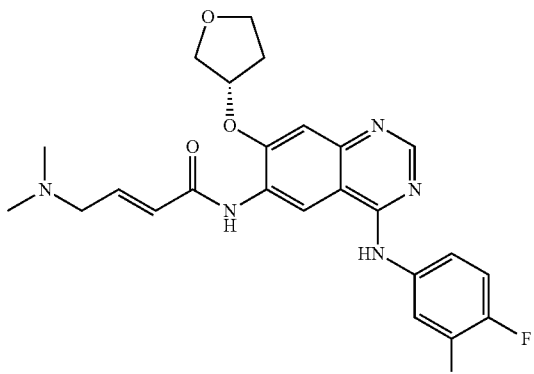

Afatinib

| Pain type | # of patients complaining pain/# of patients given afatinib | | # of patients complaining pain/# patients given placebo | |
|---|---|---|---|---|
| | Counts | Percentage(%) | Counts | Percentage(%) |
| Pain in Extremity[b] | 27/390 | 6.92 | 4/195 | 2.05 |
| Back Pain[a] | 29/390 | 7.43 | 22/195 | 11.28 |
| Headache[b] | 21/390 | 5.38 | 9/195 | 4.62 |
| Pain - chest/thorax[b] | 27/390 | 6.92 | 11/195 | 5.64 |
| Total pain occurrence[b,c] | 104/390 | 26.67 | 46/195 | 23.59 |

[a]There were less patients complaining about the pain compared to the placebo group, but the difference was not significant (p > 0.05).
[b]There were more patients complaining about the pain compared to the placebo group.
[c]The total pain occurrence may include multiple types of pain from each patient.

For arthralgia and headache, the differences are all statistically significant (p<0.05). For musculoskeletal and oral pains, the differences are not statistically significant, due to the relatively smaller sample sizes for these types of pain compared to arthralgia and headache. Nevertheless, when all of the numbers are added together to calculate the total pain occurrence as showed in pain-overall category listed in Table 5, the overall clinical data show that lapatinib indeed can significantly relieve pain in cancer patients (p<0.05).

TABLE 5

Number and percentage of patients complaining about various pains used lapatinib compared with the corresponding control drugs or placebo in clinical trials.

| Pain type | # of patients complaining pain/# of patients given lapatinib | | # of patients complaining pain/# of patients in the control group | | Pain decreased compared to control group (%) |
|---|---|---|---|---|---|
| | Counts | Percentage (%) | Counts | Percentage (%) | |
| Arthralgia[a,b] | 72/1714 | 4.20 | 119/1711 | 6.96 | 39.60 |
| Musculoskeletal Pain[b,c] | 15/490 | 3.06 | 24/473 | 5.07 | 39.67 |
| Headache[a,b,c,d] | 182/2132 | 8.54 | 231/2083 | 11.09 | 23.02 |
| Oral pain[c,d] | 35/418 | 8.37 | 38/372 | 10.22 | 18.03 |

TABLE 5-continued

Number and percentage of patients complaining about various pains used lapatinib compared with the corresponding control drugs or placebo in clinical trials.

| Pain type | # of patients complaining pain/# of patients given lapatinib | | # of patients complaining pain/# of patients in the control group | | Pain decreased compared to control group (%) |
|---|---|---|---|---|---|
| | Counts | Percentage (%) | Counts | Percentage (%) | |
| Pain-overall[a,b,c,d] | 304/4754 | 6.39 | 412/4639 | 8.88 | 28.00 |
| Myalgia[e] | 321/3314 | 9.69 | 367/3256 | 11.27 | 14.02 |

[a]Data from clinical trial NCT00374322;
[b]Data from clinical trial NCT00390455;
[c]Data from clinical trial NCT00424255;
[d]Data from clinical trial NCT00371566.
[e]Data from clinical trial NCT00558103, NCT00430781, NCT00553358, NCT00490139, NCT00073528, NCT429299, NCT00390455, NCT00524303, NCT00770809. Data of the same type of pain were combined if coming from multiple clinical trials. The pain-overall column was calculated by adding all the individual pains together. Pains with too small patient counts (n < 5) were considered statistically insignificant and not included in the table.

Figure 5A:
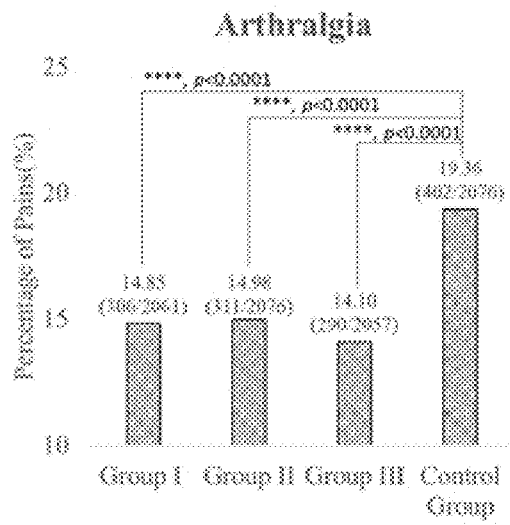
FIG. 5A-5F. Number and percentage of patients complaining about pain after using lapatinib and/or trastuzumab in clinical trial NCT00490139.
Figure 5B:
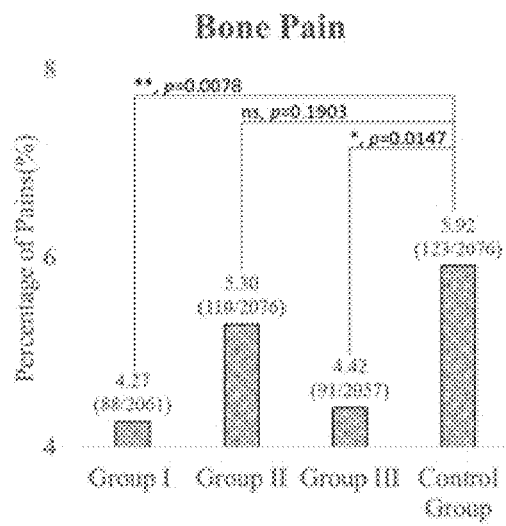
Figure 5C:
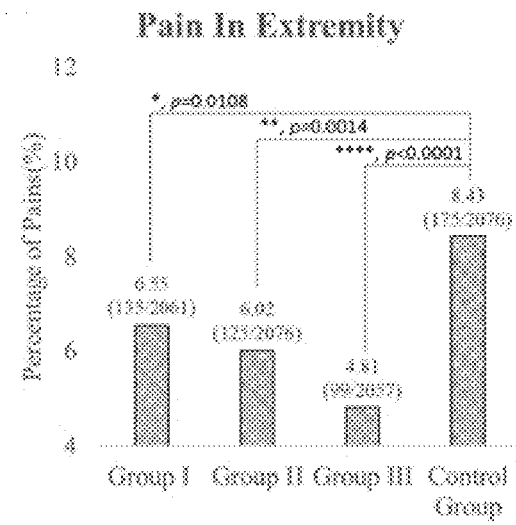
Figure 5D:
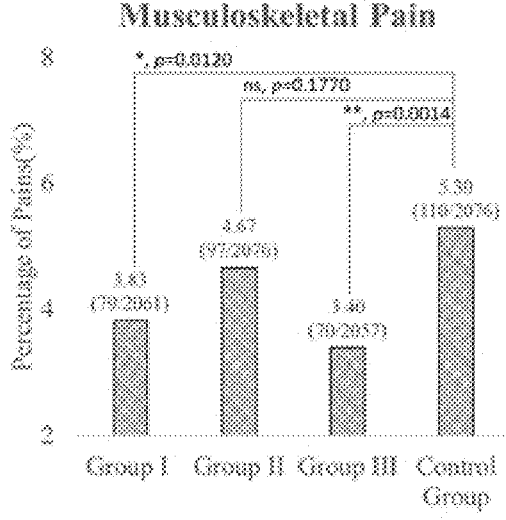
Figure 5E:
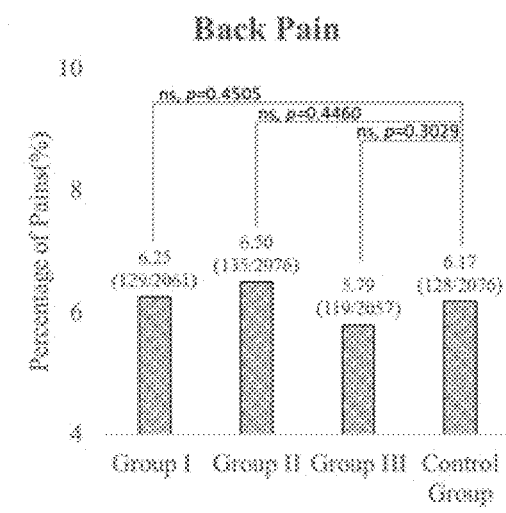
Figure 5F:
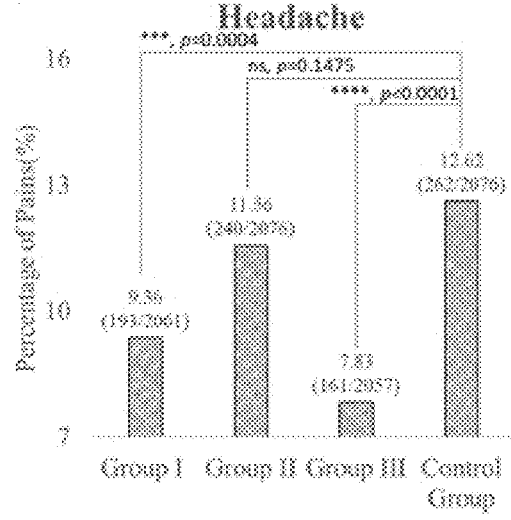

It is also interesting to note that a large-scale phase III clinical trial NCT00490139 included four groups of patients using either lapatinib or trastuzumab alone or together in different ways (see Table 6), although it did not have a dedicated placebo group. According to the data summarized in Table 6, the patients given trastuzumab together with lapatinib had significantly less complaints about various types of pain compared to the patients given only trastuzumab (FIG. 5). Based on the data shown in FIG. 5, lapatinib can significantly relive all types of pain (p<0.05), except for the back pain (p>0.05).

TABLE 6

Some useful data extracted from clinical trial NCT00490139 and the identified differences between groups in the trial.

| Pain type | Group I | | Group II | | Group III | | Control group |
|---|---|---|---|---|---|---|---|
| | Patient counts | p value[a] | Patient counts | p value[a] | Patient counts | p value[a] | Patient counts |
| Arthralgia | 306/2061 (14.85%) | <0.0001 | 311/2076 (14.98%) | <0.0001 | 290/2057 (14.10%) | <0.0001 | 402/2076 (19.36%) |
| Pain in Extremity | 135/2061 (6.55%) | 0.0108 | 125/2076 (6.02%) | 0.0014 | 99/2057 (4.81%) | <0.0001 | 175/2076 (8.43%) |
| Back Pain | 129/2061 (6.25%) | 0.4505 | 135/2076 (6.50%) | 0.4460 | 119/2057 (5.79%) | 0.3029 | 128/2076 (6.17%) |
| Bone Pain | 88/2061 (4.27%) | 0.0078 | 110/2076 (5.30%) | 0.1903 | 91/2057 (4.42%) | 0.0147 | 123/2076 (5.92%) |
| Musculoskeletal pain | 79/2061 (3.83%) | 0.0120 | 97/2076 (4.67%) | 0.1770 | 70/2057 (3.40%) | 0.0014 | 110/2076 (5.30%) |
| Headache | 193/2061 (9.36%) | 0.0004 | 240/2076 (11.56%) | 0.1475 | 161/2057 (7.83%) | <0.0001 | 262/2076 (12.62%) |

[a]The p values were calculated comparing the patient counts to the control group using $\chi^2$ tests. Group I: oral lapatinib 1000 mg daily with trastuzumab (8 mg/kg IV loading dose, followed by 6 mg/kg IV every 3 week) for 52 weeks. Group II: weekly trastuzumab for 12 weeks (4 mg/kg IV loading dose, followed by 2 mg/kg IV weekly), followed by a 6-week washout period, followed by oral lap 1500 mg daily for 34 weeks. Group III: oral lapatinib 1500 mg daily for 52 weeks. Control group: trastuzumab 8 mg/kg IV, followed by 6 mg/kg IV every 3 weeks for 52 weeks.

All clinical data analyzed above have consistently demonstrated that lapatinib indeed can serve as an effective analgesic to relive various types of pain in patients. The remaining question is whether the analgesic effects of lapatinib are really due to the inhibition of mPGES-1, rather than the dual inhibition of EGFR and HER2 because lapatinib is known as a potent inhibitor of both EGFR and HER2. To address this question, data from phase III clinical trial (NCT00656136) was also analyzed for drug afatinib, another EGFR and HER2 dual inhibitor approved by the FDA in 2013. Like lapatinib, afatinib can also similarly inhibit both EGFR and HER2. The pain information from the trial NCT00656136 are summarized in Table 2, showing that afatinib had no analgesic effects at all. These clinical data further support the conclusion that the significant analgesic effects of lapatinib are due to the mPGES-1 inhibition, rather than the EGFR/HER2 inhibition.

TABLE 7

Sources of the original clinical trial data about various types of pain in lapatinib-related clinical trials.

|  | NCT00374322[a] | NCT00390455[a] | NCT00424255[a] | NCT00371566[a] | NCT00656136[b] |
|---|---|---|---|---|---|
| Arthralgia | | | | | |
| With drug pains | 69 | 3 | | | |
| With drug total | 1573 | 141 | | | |
| With control pains | 113 | 6 | | | |
| With control total | 1574 | 137 | | | |
| Pain In Extremity | | | | | |
| With drug pains | | 1 | | | 27 |
| With drug total | | 141 | | | 390 |
| With control pains | | 4 | | | 4 |
| With control total | | 137 | | | 195 |
| Back Pain | | | | | |
| With drug pains | | 5 | | | 29 |
| With drug total | | 141 | | | 390 |
| With control pains | | 1 | | | 22 |
| With control total | | 137 | | | 195 |
| Bone Pain | | | | | |
| With drug pains | | 3 | | | |
| With drug total | | 141 | | | |
| With control pains | | 2 | | | |
| With control total | | 137 | | | |
| Musculoskeletal Pain | | | | | |
| With drug pains | | 0 | 15 | | |
| With drug total | | 141 | 349 | | |
| With control pains | | 1 | 23 | | |
| With control total | | 137 | 336 | | |
| Headache | | | | | |
| With drug pains | 140 | 19 | 20 | 3 | 21 |
| With drug total | 1573 | 141 | 349 | 69 | 390 |
| With control pains | 185 | 16 | 28 | 2 | 9 |
| With control total | 1574 | 137 | 336 | 36 | 195 |
| Pain-throat/pharynx/larynx | | | | | |
| With drug pains | | | | | 27 |
| With drug total | | | | | 390 |
| With control pains | | | | | 11 |
| With control total | | | | | 195 |
| Pain-chest/thorax | | | | | |
| With drug pains | | 1 | | | |
| With drug total | | 141 | | | |
| With control pains | | 1 | | | |
| With control total | | 137 | | | |
| Oral pain | | | | | |
| With drug pains | | | 25 | 10 | |
| With drug total | | | 349 | 69 | |
| With control pains | | | 35 | 3 | |
| With control total | | | 336 | 36 | |

[a]Lapatinib was investigated in these clinical trials.
[b]Afatinib was investigated in this clinical trial.

CONCLUSIONS AND DISCUSSION

Through computational modeling and simulations, an open conformation of human mPGES-1 was discovered in solution, which is remarkably different from the closed conformation shown in all of the reported crystal structures. The open conformation is stable only in the absence of co-factor GSH. The newly identified open conformation may serve a new target for rational design of novel inhibitors of mPGES-1.

Using the computationally identified open conformation, the further virtual screening of FDA-approved drugs, followed by in vitro activity assays have demonstrated that multiple FDA-approved drugs, including lapatinib etc., can significantly inhibit human mPGES-1. Thus, these FDA-approved drugs could also have some analgesic effects, depending on their actual pharmacokinetic profiles associated with actually used dosage forms.

In particular, within all of the mPGES-1 inhibitors identified from the FDA-approved drugs, lapatinib has been identified as the most potent one, with $IC_{50}$=~800 nM. Further clinical data mining revealed that lapatinib indeed significantly relived a variety of pain in patients whether it was used alone or in combined use with another drug in the reported clinical trials. So, lapatinib may serve as the first highly desirable non-addictive analgesic targeting mPGES-1.

Further, the scaffold of the lapatinib structure may be used as a new starting point for further rational design of a lapatinib analog which can more potently inhibit mPGES-1 without inhibiting EGFR and HER2. Such a lapatinib analog may serve as an improved analgesic compared to lapatinib itself in terms of both the efficacy and side effects. Similarly, the scaffolds of other FDA-approved drugs identified as mPGES-1 inhibitors (with the $IC_{50}$ values listed in Table S1) may also be used as new starting points for rational design of their analogs that can more potently and selectively inhibit mPGES-1.

In addition, the general DREAM-in-CDM approach may also be useful for repurposing FDA-approved drugs for other new therapeutic indications associated with the new targets.

Methods

In Silico Simulation.

The CHARMM-GUI membrane builder[60] was used for building the 3D structural model and preparing MD input files. Only the protein part with/without GSH was used for building the model. A total of 153 DOPC molecules were used to build the membrane model, and a total of 11365 water molecules were added to fill the water box. In addition, 25 sodium and 46 chloride ions are added to neutralize the system and adjust the salt concentration to 0.15 M.

The NAMD 2.10 program[61] was used to run the 100 ns long simulation. The input files were generated by the CHARMM-GUI builder, and the CHARMM force field was used in the MD simulation. The simulation temperature was set at 303.15 K and the time step used was 2 fs. The Nose-Hoover Langevin piston pressure control was used to keep the temperature and pressure constant.

The AMBER12 software was used for the TMD, PMF, and MM-PBSA simulations/calculations. Input models were generated by the NAMD simulation results. AMBER ff03 force field and lipid11 force field were used for the simulation. In the TMD study, the closed conformation state was used as the starting conformation, and the open conformation state was used as the final conformation. Along the reaction coordinate, a conformation in every 5 degrees was selected as a window. For each window, the structure was minimized and equilibrated, followed by an MD simulation (1 ns) for the conformational sampling. The obtained energetic data were then submitted to the WHAM script for the PMF calculations.

Compounds from the FDA-approved drug library were virtually screened using AutoDock Vina 1.1.2[67] and then the MM-PBSA calculations[68] to estimate the binding free energies. The compounds were then ranked by the estimated binding free energies and the ones with the highest ranking were then ordered for in vitro activity tests.

In Vitro Activity Tests.

The protocol for the protein preparation and in vitro activity assays were the same as described previously.[69-72] The enzyme activity assays were performed on ice in 1.5 ml microfuge tubes by using the expressed human mPGES-1. The reaction mixture contained: 0.2 M $Na_2HPO_4/NaH_2PO_4$, pH 7.2, 10 µL; 0.1 M GSH, 2.5 µL; diluted microsomal enzyme (80 µg/mL), 1 µL; $PGH_2$ (0.31 mM in DMF), 5 µL; 1 µL inhibitor; and $H_2O$ in a final reaction volume of 100 µL. $PGH_2$ was stored in dry ice and used to initiate the reaction. Compounds were incubated with the enzyme for 15 min at room temperature before the addition of cold $PGH_2$ (1 µM final) to initiate the enzyme reaction. After 30 s, 10 µL of $SnCl_2$ (40 mg/mL) in ethanol was added to stop the reaction. The non-enzymatic conversion of $PGH_2$ to $PGE_2$ was performed in the same buffer devoid of enzyme. The reaction mixture was placed on ice until $PGE_2$ production was determined by the $PGE_2$ enzyme immunoassay as described earlier. $IC_{50}$ values of the inhibitors were calculated by using the GraphPad Prism 6.0.

Clinical Data Mining.

All p values on the differences between groups were calculated using $\chi^2$ tests on GraphPad Prism 6.0. Confidence interval was set at 95%. One-tailed tests were performed since lapatinib was expected to have less pain occurrence compared to the corresponding control group. Barnard's tests or Fisher's tests were not chosen due to the large sample size and Yate's correction on $\chi^2$ tests was not adopted due to the same reason.

Example (Prophetic)—Clinical studies are performed in various cancer and non-cancer groups of subjects with various doses of lapatinib ranging from 50 to 1500 mg. Pain relieve efficacy is confirmed in the various cancer and non-cancer groups.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. SovereignHealth, US witnesses opioid addiction; poorest countries have no access to opioids: Study (www.sovhealth.com/addiction/us-witnesses-opioid-addiction-poorest-countries-no-access-opioids-study/—Last seen: Mar. 10, 2018). 2017.
2. ASAM, Opioid Addiction—2016 Facts & Figures (www.asam.org/docs/default-source/advocacy/opioid-addiction-disease-facts-figures.pdf; last seen: Mar. 10, 2018). 2017.
3. USDOJ, CD No. 2 ("1. Chasing the Dragon; 2. Heroin Hurts; 3. Heroin is Hell; 4. Heroin is Here; 5 Heroin's Hold"), distributed to the invited attendees of US Attorney-General Loretta E. Lynch's "National Heroin & Opioid Awareness Week" policy speech at College of Pharmacy, University of Kentucky on Sep. 20, 2016. 2016.
4. Deyo, R. A.; Korff, M. V.; Duhrkoop, D., Opioids for low back pain. *BMJ* 2015, 350, g6380. doi: doi.org/10.1136/bmj.g6380 (Published 5 Jan. 2015).
5. Nissen, S. E.; Yeomans, N. D.; Solomon, D. H.; Liischer, T. F.; Libby, P.; Husni, E.; Graham, D. Y.; Borer, J. S.;

Wisniewski, L. M.; Wolski, K. E.; Wang, Q.; Menon, V., Cardiovascular Safety of Celecoxib, Naproxen, or Ibuprofen for Arthritis. *N. Engl. J. Med.* 2016, 375, 2519-2529. DOI: 10.1056/NEJMoa1611593.
6. Felson, D. T., Safety of Nonsteroidal Antiinflammatory Drugs. *N. Engl. J. Med.* 2016, 375, 2595-2596. DOI: 10.1056/NEJMe1614257.
7. Basbaum, A. I.; Bautista, D. M.; Scherrer, G.; Julius, D., Cellular and Molecular Mechanisms of Pain. *Cell* 2009, 139, 267-284.
8. Chang, M. C.; Lin, S. I.; Lin, L. D.; Chan, C. P.; Lee, M. S.; Wang, T. M.; Jeng, P. Y.; Yeung, S. Y.; Jeng, J. H., Prostaglandin E2 Stimulates EP2, Adenylate Cyclase, Phospholipase C, and Intracellular Calcium Release to Mediate Cyclic Adenosine Monophosphate Production in Dental Pulp Cells. *J Endod.* 2016, 42, 584-588.
9. Al-Hasani, R.; Bruchas, M. R., Molecular Mechanisms of Opioid Receptor-Dependent Signaling and Behavior. *Anesthesiology* 2011, 115, 1363-1381.
10. Asher, A., Celebrex, Vioxx, Bextra vs Opioids for Back or Neck Pain www.verywell.com/cox-2-inhibitors-compared-with-opioids-297303. 2017.
11. Manglik, A.; Lin, H.; Aryal, D. K.; McCorvy, J. D.; Dengler, D.; Corder, G.; Levit, A.; Kling, R. C.; Bernat, V.; Hubner, H.; Huang, X.-P.; Sassano, M. F.; Giguère, P. M.; Löber, S.; Duan, D.; Scherrer, G.; Kobilka, B. K.; Gmeiner, P.; Roth, B. L.; Shoichet, B. K., Structure-based discovery of opioid analgesics with reduced side effects. *Nature* 2016, 537, 185-190. doi: 10.1038/nature19112.
12. Che, T.; Majumdar, S.; Zaidi, S. A.; Ondachi, P.; McCorvy, J. D.; Wang, S.; Mosier, P. D.; Uprety, R.; Vardy, E.; Krumm, B. E.; Han, G. W.; Lee, M.-Y.; Pardon, E.; Steyaert, J.; Huang, X.-P.; Strachan, R. T.; Tribo, A. R.; Pasternak, G. W.; Carroll, F. I.; Stevens, R. C.; Cherezov, V.; Katritch, V.; Wacker, D.; Roth, B. L., Structure of the Nanobody-Stabilized Active State of the Kappa Opioid Receptor. *Cell* 2018, 172, 55-67.
13. Healy, J. R.; Bezawada, P.; Griggs, N. W.; Devereaux, A. L.; Matsumoto, R. R.; Traynor, J. R.; Coop, A.; Cunningham, C. W., Benzylideneoxymorphone: A new lead for development of bifunctional mu/delta opioid receptor ligands. *Bioorg. Med. Chem. Lett.* 2017, 27, 666-669.
14. Ding, H.; Czoty, P. W.; Kiguchi, N.; Cami-Kobeci, G.; Sukhtankar, D. D.; Nader, M. A.; Husbands, S. M.; Ko, M.-C., A novel orvinol analog, BU08028, as a safe opioid analgesic without abuse liability in primates. *Proc. Natl Acad. Sci. USA* 2016, 113, E5511-8. doi: 10.1073/pnas.1605295113.
15. Hamza, A.; Zhao, X.; Tong, M.; Tai, H.-H.; Zhan, C.-G., Novel human mPGES-1 inhibitors identified through structure-based virtual screening. *Bioorg. Med. Chem.* 2011, 19, 6077-6086.
16. Zhou, Z.; Yuan, Y.; Zhou, S.; Ding, K.; Zheng, F.; Zhan, C.-G., Selective inhibitors of human mPGES-1 from structure-based computational screening. *Biorg. Med. Chem. Letters* 2017, 27, 3739-3743.
17. Ding, K.; Zhou, Z.; Zhou, S.; Yuan, Y.; Kim, K.; Zhang, T.; Zheng, X.; Zheng, F.; Zhan, C.-G., Design, synthesis, and discovery of 5-((1,3-diphenyl-1H-pyrazol-4-yl)methylene)pyrimidine-2,4,6(1H,3H,5H)-triones and related derivatives as novel inhibitors of mPGES-1. *Bioorg. Med. Chem. Letters* 2018, 28, 858-862.
18. Zhan, C.-G.; Zheng, F.; Ding, K.; Zhou, Z., PCT/US2017/039785: No. WO2018/005660. "Prostaglandin E Synthase Inhibitors and Methods for Utilizing the Same" (World Patent filed on Jun. 28, 2017). 2017.
19. Ding, K.; Zhou, Z.; Hou, S.; Yuan, Y.; Zhou, S.; Zheng, X.; Chen, J.; Loftin, C.; Zheng, F.; Zhan, C.-G., Structure-based discovery of mPGES-1 inhibitors suitable for preclinical testing in wild-type mice as a new generation of anti-inflammatory drugs. *Scientific Reports* 2018, 8, 5205. doi:10.1038/s41598-018-23482-4.
20. Koeberle, A.; Laufer, S. A.; Werz, O., Design and Development of Microsomal Prostaglandin E2 Synthase-1 Inhibitors: Challenges and Future Directions. *J. Med. Chem.* 2016, 59, 5970-5986.
21. Meunier, L.; Larrey, D., Recent Advances in Hepatotoxicity of Non Steroidal Anti-Inflammatory Drugs. *Ann. Hepatol.* 2018, 17, 187-191.
22. Strawson, J Nonsteroidal anti-inflammatory drugs and cancer pain. *Curr. Opin Support Palliat Care* 2018, doi: 10.1097/SPC.0000000000000332 [Epub ahead of print: Feb. 9, 2018].
23. Thomas, K.; Moody, T. W.; Jensen, R. T.; Tong, J.; Rayner, C. L.; Barnett, N. L.; Fairfull-Smith, K. E.; Ridnour, L. A.; Wink, D. A.; Bottle, S. E., Design, synthesis and biological evaluation of hybrid nitroxide-based non-steroidal anti-inflammatory drugs. *Eur. J. Med. Chem.* 2018, 147, 34-47.
24. Kudo, I.; Murakami, M., Prostaglandin E synthase, a terminal enzyme for prostaglandin E-2 biosynthesis. *Journal of Biochemistry and Molecular Biology* 2005, 38 (6), 633-638.
25. Serhan, C. N.; Levy, B., Success of prostaglandin E-2 in structure-function is a challenge for structure-based therapeutics. *Proceedings of the National Academy of Sciences of the United States of America* 2003, 100 (15), 8609-8611.
26. Radmark, O.; Samuelsson, B., Microsomal prostaglandin E synthase-1 and 5-lipoxygenase: potential drug targets in cancer. *J. Intern. Med.* 2010, 268, 5-14.
27. Hanaka, H.; Pawelzik, S.-C.; Johnsen, J. I.; Rakonjac, M.; Terawaki, K.; Rasmuson, A.; Sveinbjornsson, B.; Schumacher, M. C.; Hamberg, M.; Samuelsson, B.; Jakobsson, P.-J.; Kogner, P.; Rådmark, O., Microsomal prostaglandin E synthase 1 determines tumor growth in vivo of prostate and lung cancer cells. *Proc. Natl. Acad. Sci. USA* 2009, 106, 18757-18762.
28. Koeberle, A.; Werz, O., Perspective of microsomal prostaglandin E2 synthase-1 as drug target in inflammation-related disorders. *Biochem. Pharmacol.* 2015, 98, 1-15.
29. Fahmi, H., MPGES-1 as a novel target for arthritis. *Current Opinion in Rheumatology* 2004, 16 (5), 623-627.
30. Tanioka, T.; Nakatani, Y.; Semmyo, N.; Murakami, M.; Kudo, I., Molecular identification of cytosolic prostaglandin E2 synthase that is functionally coupled with cyclooxygenase-1 in immediate prostaglandin E2 biosynthesis. *J. Biol. Chem.* 2000, 275 (42), 32775-82.
31. Cheng, Y.; Wang, M.; Yu, Y.; Lawson, J.; Funk, C. D.; FitzGerald, G. A., Cyclooxygenases, microsomal prostaglandin E synthase-1, and cardiovascular function. *Journal of Clinical Investigation* 2006, 116 (5), 1391-1399.
32. Engblom, D.; Saha, S.; Engstrom, L.; Westman, M.; Audoly, L. P.; Jakobsson, P. J.; Blomqvist, A., Microsomal prostaglandin E synthase-1 is the central switch during immune-induced pyresis. *Nature Neuroscience* 2003, 6 (11), 1137-1138.
33. Trebino, C. E.; Stock, J. L.; Gibbons, C. P.; Naiman, B. M.; Wachtmann, T. S.; Umland, J. P.; Pandher, K.; Lapointe, J. M.; Saha, S.; Roach, M. L.; Carter, D.; Thomas, N. A.; Durtschi, B. A.; McNeish, J. D.; Hambor, J. E.; Jakobsson, P. J.; Carty, T. J.; Perez, J. R.; Audoly, L.

P., Impaired inflammatory and pain responses in mice lacking an inducible prostaglandin E synthase. *Proceedings of the National Academy of Sciences of the United States of America* 2003, 100 (15), 9044-9049.
34. Ikeda-Matsuo, Y.; Ota, A.; Fukada, T.; Uematsu, S.; Akira, S.; Sasaki, Y., Microsomal prostaglandin E synthase-1 is a critical factor of stroke-reperfusion injury. *Proceedings of the National Academy of Sciences of the United States of America* 2006, 103 (31), 11790-11795.
35. Friesen, R. W.; Mancini, J. A., Microsomal prostaglandin E-2 synthase-1 (mPGES-1): A novel anti-inflammatory therapeutic target. *Journal of medicinal chemistry* 2008, 51 (14), 4059-4067.
36. Schiffler, M. A.; Antonysamy, S.; Bhattachar, S. N.; Campanale, K. M.; Chandrasekhar, S.; Condon, B.; Desai, P. V.; Fisher, M. J.; Groshong, C.; Harvey, A.; Hickey, M. J.; Hughes, N. E.; Jones, S. A.; Kim, E. J.; Kuklish, S. L.; Luz, J. G.; Norman, B. H.; Rathmell, R. E.; Rizzo, J. R.; Seng, T. W.; Thibodeaux, S. J.; Woods, T. A.; York, J. S.; Yu, X. P., Discovery and Characterization of 2-Acylaminoimidazole Microsomal Prostaglandin E Synthase-1 Inhibitors. *Journal of medicinal chemistry* 2016, 59 (1), 194-205.
37. Hieke, M.; Greiner, C.; Dittrich, M.; Reisen, F.; Schneider, G.; Schubert-Zsilavecz, M.; Werz, O., Discovery and biological evaluation of a novel class of dual microsomal prostaglandin E2 synthase-1/5-lipoxygenase inhibitors based on 2-[(4,6-diphenethoxypyrimidin-2-yl)thio] hexanoic acid. *Journal of medicinal chemistry* 2011, 54 (13), 4490-507.
38. Hanke, T.; Dehm, F.; Liening, S.; Popella, S. D.; Maczewsky, J.; Pillong, M.; Kunze, J.; Weinigel, C.; Barz, D.; Kaiser, A.; Wurglics, M.; Lammerhofer, M.; Schneider, G.; Sautebin, L.; Schubert-Zsilavecz, M.; Werz, O., Aminothiazole-featured pirinixic acid derivatives as dual 5-lipoxygenase and microsomal prostaglandin E2 synthase-1 inhibitors with improved potency and efficiency in vivo. *Journal of medicinal chemistry* 2013, 56 (22), 9031-44.
39. Terracciano, S.; Lauro, G.; Strocchia, M.; Fischer, K.; Werz, O.; Riccio, R.; Bruno, I.; Bifulco, G., Structural Insights for the Optimization of Dihydropyrimidin-2(1H)-one Based mPGES-1 Inhibitors. *ACS medicinal chemistry letters* 2015, 6 (2), 187-91.
40. Shiro, T.; Kakiguchi, K.; Takahashi, H.; Nagata, H.; Tobe, M., 7-Phenyl-imidazoquinolin-4(5H)-one derivatives as selective and orally available mPGES-1 inhibitors. *Bioorganic & medicinal chemistry* 2013, 21 (11), 2868-78.
41. Shiro, T.; Kakiguchi, K.; Takahashi, H.; Nagata, H.; Tobe, M., Synthesis and biological evaluation of substituted imidazoquinoline derivatives as mPGES-1 inhibitors. *Bioorganic & medicinal chemistry* 2013, 21 (7), 2068-78.
42. Shiro, T.; Takahashi, H.; Kakiguchi, K.; Inoue, Y.; Masuda, K.; Nagata, H.; Tobe, M., Synthesis and SAR study of imidazoquinolines as a novel structural class of microsomal prostaglandin E(2) synthase-1 inhibitors. *Bioorg Med Chem Lett* 2012, 22 (1), 285-8.
43. Liedtke, A. J.; Keck, P. R.; Lehmann, F.; Koeberle, A.; Werz, O.; Laufer, S. A., Arylpyrrolizines as inhibitors of microsomal prostaglandin E2 synthase-1 (mPGES-1) or as dual inhibitors of mPGES-1 and 5-lipoxygenase (5-LOX). *Journal of medicinal chemistry* 2009, 52 (15), 4968-72.
44. Shang, E.; Wu, Y.; Liu, P.; Liu, Y.; Zhu, W.; Deng, X.; He, C.; He, S.; Li, C.; Lai, L., Benzo[d]isothiazole 1,1-dioxide derivatives as dual functional inhibitors of 5-lipoxygenase and microsomal prostaglandin E(2) synthase-1. *Bioorg Med Chem Lett* 2014, 24 (12), 2764-7.
45. Wu, T. Y.; Juteau, H.; Ducharme, Y.; Friesen, R. W.; Guiral, S.; Dufresne, L.; Poirier, H.; Salem, M.; Riendeau, D.; Mancini, J.; Brideau, C., Biarylimidazoles as inhibitors of microsomal prostaglandin E2 synthase-1. *Bioorg Med Chem Lett* 2010, 20 (23), 6978-82.
46. Wiegard, A.; Hanekamp, W.; Griessbach, K.; Fabian, J.; Lehr, M., Pyrrole alkanoic acid derivatives as nuisance inhibitors of microsomal prostaglandin E2 synthase-1. *European journal of medicinal chemistry* 2012, 48, 153-63.
47. Chini, M. G.; De Simone, R.; Bruno, I.; Riccio, R.; Dehm, F.; Weinigel, C.; Barz, D.; Werz, O.; Bifulco, G., Design and synthesis of a second series of triazole-based compounds as potent dual mPGES-1 and 5-lipoxygenase inhibitors. *European journal of medicinal chemistry* 2012, 54, 311-23.
48. Giroux, A.; Boulet, L.; Brideau, C.; Chau, A.; Claveau, D.; Cote, B.; Ethier, D.; Frenette, R.; Gagnon, M.; Guay, J.; Guiral, S.; Mancini, J.; Martins, E.; Masse, F.; Methot, N.; Riendeau, D.; Rubin, J.; Xu, D.; Yu, H.; Ducharme, Y.; Friesen, R. W., Discovery of disubstituted phenanthrene imidazoles as potent, selective and orally active mPGES-1 inhibitors. *Bioorg Med Chem Lett* 2009, 19 (20), 5837-41.
49. Xu, D.; Rowland, S. E.; Clark, P.; Giroux, A.; Cote, B.; Guiral, S.; Salem, M.; Ducharme, Y.; Friesen, R. W.; Methot, N.; Mancini, J.; Audoly, L.; Riendeau, D., MF63 [2-(6-chloro-1H-phenanthro[9,10-d]imidazol-2-yl)-isophthalonitrile], a selective microsomal prostaglandin E synthase-1 inhibitor, relieves pyresis and pain in preclinical models of inflammation. *J. Pharmacol. Exp. Ther.* 2008, 326 (3), 754-63.
50. Lee, K.; Pham, V. C.; Choi, M. J.; Kim, K. J.; Lee, K. T.; Han, S. G.; Yu, Y. G.; Lee, J. Y., Fragment-based discovery of novel and selective mPGES-1 inhibitors Part 1: identification of sulfonamido-1,2,3-triazole-4,5-dicarboxylic acid. *Bioorg Med Chem Lett* 2013, 23 (1), 75-80.
51. Cote, B.; Boulet, L.; Brideau, C.; Claveau, D.; Ethier, D.; Frenette, R.; Gagnon, M.; Giroux, A.; Guay, J.; Guiral, S.; Mancini, J.; Martins, E.; Masse, F.; Methot, N.; Riendeau, D.; Rubin, J.; Xu, D.; Yu, H.; Ducharme, Y.; Friesen, R. W., Substituted phenanthrene imidazoles as potent, selective, and orally active mPGES-1 inhibitors. *Bioorg Med Chem Lett* 2007, 17 (24), 6816-20.
52. Riendeau, D.; Aspiotis, R.; Ethier, D.; Gareau, Y.; Grimm, E. L.; Guay, J.; Guiral, S.; Juteau, H.; Mancini, J. A.; Methot, N.; Rubin, J.; Friesen, R. W., Inhibitors of the inducible microsomal prostaglandin E2 synthase (mPGES-1) derived from MK-886. *Bioorg Med Chem Lett* 2005, 15 (14), 3352-5.
53. Bruno, A.; Di Francesco, L.; Coletta, I.; Mangano, G.; Alisi, M. A.; Polenzani, L.; Milanese, C.; Anzellotti, P.; Ricciotti, E.; Dovizio, M.; Di Francesco, A.; Tacconelli, S.; Capone, M. L.; Patrignani, P., Effects of AF3442 [N-(9-ethyl-9H-carbazol-3-yl)-2-(trifluoromethyl)benzamide], a novel inhibitor of human microsomal prostaglandin E synthase-1, on prostanoid biosynthesis in human monocytes in vitro. *Biochem Pharmacol* 2010, 79 (7), 974-81.
54. Koeberle, A.; Haberl, E. M.; Rossi, A.; Pergola, C.; Dehm, F.; Northoff, H.; Troschuetz, R.; Sautebin, L.; Werz, O., Discovery of benzo[g]indol-3-carboxylates as potent inhibitors of microsomal prostaglandin E(2) synthase-1. *Bioorganic & medicinal chemistry* 2009, 17 (23), 7924-32.
55. Walker, D. P.; Arhancet, G. B.; Lu, H. F.; Heasley, S. E.; Metz, S.; Kablaoui, N. M.; Franco, F. M.; Hanau, C. E.; Scholten, J. A.; Springer, J. R.; Fobian, Y. M.; Carter, J. S.; Xing, L.; Yang, S.; Shaffer, A. F.; Jerome, G. M.; Baratta, M. T.; Moore, W. M.; Vazquez, M. L., Synthesis and biological evaluation of substituted benzoxazoles as inhibitors of mPGES-1: use of a conformation-based hypothesis to facilitate compound design. *Bioorg Med Chem Lett* 2013, 23 (4), 1120-6.
56. Wang, J.; Limburg, D.; Carter, J.; Mbalaviele, G.; Gierse, J.; Vazquez, M., Selective inducible microsomal prostaglandin E(2) synthase-1 (mPGES-1) inhibitors derived from an oxicam template. *Bioorg Med Chem Lett* 2010, 20 (5), 1604-9.
57. Jin, Y.; Smith, C. L.; Hu, L.; Campanale, K. M.; Stoltz, R.; Huffman, L. G., Jr.; McNearney, T. A.; Yang, X. Y.; Ackermann, B. L.; Dean, R.; Regev, A.; Landschulz, W., Pharmacodynamic comparison of LY3023703, a novel microsomal prostaglandin e synthase 1 inhibitor, with celecoxib. *Clinical pharmacology and therapeutics* 2016, 99 (3), 274-84.
58. Sjogren, T.; Nord, J.; Ek, M.; Johansson, P.; Liu, G.; Geschwindner, S., Crystal structure of microsomal prostaglandin E2 synthase provides insight into diversity in the MAPEG superfamily. *Proceedings of the National Academy of Sciences of the United States of America* 2013, 110 (10), 3806-11.
59. Weinert, T.; Olieric, V.; Waltersperger, S.; Panepucci, E.; Chen, L.; Zhang, H.; Zhou, D.; Rose, J.; Ebihara, A.; Kuramitsu, S.; Li, D.; Howe, N.; Schnapp, G.; Pautsch, A.; Bargsten, K.; Prota, A. E.; Surana, P.; Kottur, J.; Nair, D. T.; Basilico, F.; Cecatiello, V.; Pasqualato, S.; Boland, A.; Weichenrieder, O.; Wang, B. C.; Steinmetz, M. O.; Caffrey, M.; Wang, M., Fast native-SAD phasing for routine macromolecular structure determination. *Nat. Methods* 2015, 12 (2), 131-3.
60. Jo, S.; Lim, J. B.; Klauda, J. B.; Im, W., CHARMM-GUI Membrane Builder for mixed bilayers and its application to yeast membranes. *Biophys.* 1 2009, 97 (1), 50-8.
61. Phillips, J. C.; Braun, R.; Wang, W.; Gumbart, J.; Tajkhorshid, E.; Villa, E.; Chipot, C.; Skeel, R. D.; Kale, L.; Schulten, K., Scalable molecular dynamics with NAMD. *Journal of computational chemistry* 2005, 26 (16), 1781-802.
62. Grossfield, A. *WHAM: the weighted histogram analysis method*, 2.0.
63. Bence, A. K.; Anderson, E. B.; Halepota, M. A.; Doukas, M. A.; DeSimone, P. A.; Davis, G. A.; Smith, D. A.; Koch, K. M.; Stead, A. G.; Mangum, S.; Bowen, C. J.; Spector, N. L.; Hsieh, S.; Adams, V. R., Phase I pharmacokinetic studies evaluating single and multiple doses of oral GW572016, a dual EGFR-ErbB2 inhibitor, in healthy subjects. *Invest New Drugs* 2005, 23 (1), 39-49.
64. Hudachek, S. F.; Gustafson, D. L., Physiologically based pharmacokinetic model of lapatinib developed in mice and scaled to humans. *J Pharmacokinet Pharmacodyn* 2013, 40 (2), 157-76.
65. Kaufman, B.; Wu, Y.; Amonkar, M. M.; Sherrill, B.; Bachelot, T.; Salazar, V.; Viens, P.; Johnston, S., Impact of lapatinib monotherapy on QOL and pain symptoms in patients with HER2+ relapsed or refractory inflammatory breast cancer. *Curr Med Res Opin* 2010, 26 (5), 1065-73.
66. Goss, P. E.; Smith, I. E.; O'Shaughnessy, J.; Ejlertsen, B.; Kaufmann, M.; Boyle, F.; Buzdar, A. U.; Fumoleau, P.; Gradishar, W.; Martin, M.; Moy, B.; Piccart-Gebhart, M.; Pritchard, K. I.; Lindquist, D.; Chavarri-Guerra, Y.; Aktan, G.; Rappold, E.; Williams, L. S.; Finkelstein, D. M.; investigators, T., Adjuvant lapatinib for women with early-stage HER2-positive breast cancer: a randomised, controlled, phase 3 trial. *The Lancet. Oncology* 2013, 14 (1), 88-96.
67. Trott, O.; Olson, A. J., AutoDock Vina: improving the speed and accuracy of docking with a new scoring function, efficient optimization, and multithreading. *Journal of computational chemistry* 2010, 31 (2), 455-61.
68. Miller, B. R., 3rd; McGee, T. D., Jr.; Swails, J. M.; Homeyer, N.; Gohlke, H.; Roitberg, A. E., MMPBSA.py: An Efficient Program for End-State Free Energy Calculations. *J Chem Theory Comput* 2012, 8 (9), 3314-21.
69. Zhou, Z.; Yuan, Y.; Zhou, S.; Ding, K.; Zheng, F.; Zhan, C. G., Selective inhibitors of human mPGES-1 from structure-based computational screening. *Bioorg. Med. Chem. Lett.* 2017, 27 (16), 3739-3743.
70. Hamza, A.; Tong, M.; AbdulHameed, M. D.; Liu, J.; Goren, A. C.; Tai, H. H.; Zhan, C. G., Understanding microscopic binding of human microsomal prostaglandin E synthase-1 (mPGES-1) trimer with substrate PGH2 and cofactor GSH: insights from computational alanine scanning and site-directed mutagenesis. *J Phys Chem B.* 2010, 114 (16), 5605-16.
71. Huang, X. Q.; Yan, W. L.; Gao, D. Q.; Tong, M.; Tai, H.-H.; Zhan, C.-G., Structural and functional characterization of human microsomal prostaglandin E synthase-1 by computational modeling and site-directed mutagenesis. *Bioorg. Med. Chem.* 2006, 14, 3553-3562.
72. Hamza, A.; Zhao, X.; Tong, M.; Tai, H. H.; Zhan, C. G., Novel human mPGES-1 inhibitors identified through structure-based virtual screening. *Bioorg. Med. Chem.* 2011, 19 (20), 6077-86.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating pain, comprising:
    identifying a subject in need of treatment for pain, for whom opioids or nonsteroidal anti-inflammatory drugs (NSAIDs) are contraindicated; and
    administering an effective amount of lapatinib or a pharmaceutically-acceptable salt thereof to the subject.
2. The method of claim 1, and further comprising identifying the subject has having a need for analgesia.
3. The method of claim 1, wherein the pain is chronic.
4. The method of claim 1, wherein the pain is acute.
5. The method of claim 1, wherein the pain is selected from the group consisting of arthralgia (pain in joint), bone pain, pain in an extremity (limb), musculoskeletal pain, and headache.
6. The method of claim 1, wherein the subject does not have cancer.
7. The method of claim 1, wherein opioids are contraindicated for the subject.
8. The method of claim 1, wherein the subject is identified as having a contraindication to opioids when the subject has a history of or a current substance use disorder, a history of or a current alcohol addiction, a history of or a current opioid addiction or opioid use disorder (OUD), or is suspected of opioid misuse.

9. The method of claim 1, wherein the subject is identified as having a contraindication to opioids when the subject is taking a drug capable of inducing life-limiting drug-drug interaction with opioids.

10. The method of claim 9, wherein the subject is receiving a monoamine oxidase inhibitor (MAOI), propoxyphene, or a central nervous system depressant.

11. The method of claim 1, wherein the subject is identified as having a contraindication to opioids when the subject has an allergy or sensitivity to opioids.

12. The method of claim 1, wherein nonsteroidal anti-inflammatory drugs (NSAIDs) are contraindicated for the subject.

13. The method of claim 12, wherein the subject is identified as having a contraindication to NSAIDs when the subject has one or more of the following conditions: cardiovascular disease, cerebrovascular disease, myocardial infarction, transient ischemic attack, stroke, coronary artery disease, coronary artery bypass surgery, congestive heart failure, and history thereof or risk thereof.

14. The method of claim 12, wherein the subject is identified as having a contraindication to NSAIDs when the subject has one or more of the following conditions: peptic ulcer or stomach bleeding, uncontrolled hypertension, kidney disease, Irritable bowel syndrome, inflammatory bowel disease, Crohn's disease, ulcerative colitis, a prior gastric bypass surgery, a family history of gastrointestinal (GI) problems.

15. The method of claim 12, wherein the subject is identified as having a contraindication to NSAIDs when the subject is pregnant.

16. The method of claim 15, wherein the subject is in the third trimester of pregnancy.

17. The method of claim 12, wherein the subject is identified as having a contraindication to NSAIDs when the subject has an allergy or sensitivity to nonsteroidal anti-inflammatory drugs (NSAIDs).

* * * * *